US010813742B2

(12) United States Patent
Adams et al.

(10) Patent No.: US 10,813,742 B2
(45) Date of Patent: *Oct. 27, 2020

(54) JOINT KINEMATIC RECONSTRUCTION TECHNIQUES

(71) Applicant: ARTHREX, INC., Naples, FL (US)

(72) Inventors: Christopher Adams, Naples, FL (US); Alan Hirahara, Gold River, CA (US); Thomas Dooney, Jr., Naples, FL (US); Stephen S. Burkhart, Boerne, TX (US)

(73) Assignee: ARTHREX, INC., Naples, FL (US)

( * ) Notice: Subject to any disclaimer, the term of this patent is extended or adjusted under 35 U.S.C. 154(b) by 52 days.

This patent is subject to a terminal disclaimer.

(21) Appl. No.: 15/984,543

(22) Filed: May 21, 2018

(65) Prior Publication Data

US 2018/0263755 A1    Sep. 20, 2018

Related U.S. Application Data

(63) Continuation-in-part of application No. 14/872,194, filed on Oct. 1, 2015, now Pat. No. 10,172,703.

(51) Int. Cl.
*A61F 2/08* (2006.01)
*A61B 17/04* (2006.01)
*A61B 17/34* (2006.01)
*A61B 90/00* (2016.01)

(52) U.S. Cl.
CPC ........ *A61F 2/0811* (2013.01); *A61B 17/0401* (2013.01); *A61B 17/3423* (2013.01); *A61B 17/0483* (2013.01); *A61B 2017/044* (2013.01); *A61B 2017/0404* (2013.01); *A61B 2017/0441* (2013.01); *A61B 2017/0443* (2013.01); *A61B 2017/0464* (2013.01); *A61B 2090/061* (2016.02); *A61F 2002/0882* (2013.01)

(58) Field of Classification Search
CPC .................................................. A61B 17/0401
See application file for complete search history.

(56) References Cited

U.S. PATENT DOCUMENTS

| 8,231,653 | B2 | 7/2012 | Dreyfuss |
| 8,597,336 | B2 | 12/2013 | van der Burg et al. |
| 8,668,718 | B2 | 3/2014 | Euteneuer et al. |
| 8,690,960 | B2 | 4/2014 | Hotter et al. |
| 2007/0288023 | A1* | 12/2007 | Pellegrino .......... A61B 17/0401 606/232 |
| 2008/0027470 | A1 | 1/2008 | Hart et al. |
| 2008/0188936 | A1 | 8/2008 | Ball et al. |
| 2009/0156997 | A1 | 6/2009 | Trenhaile |

(Continued)

OTHER PUBLICATIONS

Declaration of Alan M. Hirahara, M.D. pursuant to 37 C.F.R. 1.32 (submitted in the parent U.S. Appl. No. 14/872,194). (Year: 2014).*

(Continued)

*Primary Examiner* — Bruce E Snow
(74) *Attorney, Agent, or Firm* — Carlson, Gaskey & Olds

(57) ABSTRACT

Methods for reconstructing a joint include fixating at least one suture inside a joint space, retrieving the at least one suture from inside the joint space, passing the at least one suture through a graft at a location external to the joint space, shuttling the graft into the joint space, and fixating the graft to bone using the at least one suture.

20 Claims, 24 Drawing Sheets

(56) References Cited

U.S. PATENT DOCUMENTS

2012/0265219 A1    10/2012  Rushdy et al.

OTHER PUBLICATIONS

ArtroCologne, Abstract Book, 2nd International Symposium on Operative and biologic Treatments in Sports Medicine, Jun. 15-16, 2007, Cologne, Germany.
Koo, et al., "Arthroscopic Double-Pulley Remplilssage Technique for Engaging Hill-Sachs Lesions in Anterior Shoulder Instability Repairs," Arthroscopy: The Journal of Arthroscopic and Related surgery, vol. 5, No. 11 Nov. 2009; pp. 1343-1348.
Mihata, et al., "Superior Capsule Reconstruction to Restore Superior Stability in Irreparable Rotator Cuff Tears: A Biomechanical Cadaveric Study," The American Journal of Sports Medicine, http://ajs.sagepub.com/.
Burkhart, et al., "The Cowboy's Campanion, A Trail Guide for the Arthroscopic Shoulder Surgeon," Wolters Kluwer/Lippincott Williams & Wilkins.
Millett, "Arthroscopic Superior Capsular Reconstruction (ASCR) Procedure," The Steadman Clinic, http://drmillet.com/massive-rotator-cuff-tear-ascr-arthroscopic-superior . . . .
Arrigoni, et al., "The Double-Pulley Technique for Double-Row Rotator Cuff Repair," Arthroscopy: The Journal of Arthroscopic and Related Surgery, vol. 23, No. 6 Jun. 2007; pp. 675.e1-675.e4.

* cited by examiner

JOINT KINEMATIC RECONSTRUCTION TECHNIQUES

CROSS-REFERENCE TO RELATED APPLICATIONS

This is a continuation-in-part of U.S. patent application Ser. No. 14/872,194, which was filed on Oct. 1, 2015, the entire disclosure of which is incorporated herein by reference.

BACKGROUND

This disclosure relates to surgical techniques for improving the joint kinematics of unstable joints using graft tissue.

Normal joint kinematics are achieved through balanced soft tissues that surround the articulating bones of a joint. An unstable joint can occur if there is significant disruption of the articulating bones or the surrounding soft tissues. The resulting joint instability may cause pain, dysfunction, accelerated bone loss, soft tissue tears and premature arthritis. Unstable joints can also occur within a replaced joint subsequent to an arthroplasty procedure.

SUMMARY

This disclosure details reconstruction techniques for improving the joint kinematics of an unstable joint. Exemplary reconstruction techniques include fixating a graft to the articulating bones of the joint using appropriately placed sutures.

A method for reconstructing a joint according to an exemplary aspect of the present disclosure includes, among other things, fixating at least one suture inside a joint space, retrieving the at least one suture from inside the joint space, passing the at least one suture through a graft at a location external to the joint space, shuttling the graft into the joint space and fixating the graft using the at least one suture.

In a further non-limiting embodiment of the foregoing method, the method includes inserting a first suture anchor and a second suture anchor into a first bone, inserting a third suture anchor and a fourth suture anchor into a second bone, measuring a first distance between the first suture anchor and the second suture anchor and a second distance between the third suture anchor and the fourth suture anchor and sizing the graft based on the first distance and the second distance.

In a further non-limiting embodiment of either of the foregoing methods, the first bone is a glenoid of a scapula and the second bone is a humerus.

In a further non-limiting embodiment of any of the foregoing methods, the method includes securing the graft to the first bone and the second bone using sutures connected to the first suture anchor, the second suture anchor, the third suture anchor and the fourth suture anchor.

In a further non-limiting embodiment of any of the foregoing methods, the method includes measuring a third distance between the first suture anchor and the third suture anchor and a fourth distance between the second suture anchor and the fourth suture anchor and sizing the graft based on the first distance, the second distance, the third distance and the fourth distance.

In a further non-limiting embodiment of any of the foregoing methods, fixating the at least one suture inside the joint space includes mounting the at least one suture to a bone using a suture anchor.

In a further non-limiting embodiment of any of the foregoing methods, the method includes punching a hole through the graft prior to passing the at least one suture through the graft.

In a further non-limiting embodiment of any of the foregoing methods, the method includes fixating multiple suture anchors inside the joint space, taking multiple measurements between the multiple suture anchors, and sizing the graft based on the multiple measurements.

In a further non-limiting embodiment of any of the foregoing methods, sizing the graft includes making the graft larger than the size indicated by the multiple measurements.

In a further non-limiting embodiment of any of the foregoing methods, the method includes marking the graft to indicate the location where each of a plurality of sutures connected to the multiple suture anchors are to pass through the graft.

In a further non-limiting embodiment of any of the foregoing methods, the method includes grasping a first suture of the plurality of sutures, pulling the first suture out of the joint space, passing the first suture through the graft, repeating the grasping, pulling and passing steps with a second suture of the plurality of sutures, and shuttling the graft into the joint space using the first suture and the second suture.

In a further non-limiting embodiment of any of the foregoing methods, the at least one suture includes multiple sutures and the multiple sutures are used to shuttle the graft inside the joint space.

In a further non-limiting embodiment of any of the foregoing methods, the graft is shuttled by the multiple sutures using a pulley technique.

In a further non-limiting embodiment of any of the foregoing methods, fixating the graft includes attaching the graft to a bone by tying a knot in the at least one suture.

In a further non-limiting embodiment of any of the foregoing methods, fixating the graft includes attaching the graft to a bone using one or more suture anchors mounted in the bone.

In a further non-limiting embodiment of any of the foregoing methods, reconstructing the joint includes reconstructing a superior capsule of a shoulder joint that includes a massive irreparable and large to massive reparable rotator cuff tears.

A method for reconstructing a joint according to another exemplary aspect of the present disclosure includes, among other things, performing either an anterior capsular reconstruction or a posterior capsular reconstruction of a shoulder joint to improve joint kinematics.

In a further non-limiting embodiment of the foregoing methods, performing the anterior capsular reconstruction or the posterior capsular reconstruction includes implanting a graft inside the shoulder joint.

In a further non-limiting embodiment of either of the foregoing methods, the method includes securing the graft to articulating bones of the shoulder joint using sutures.

In a further non-limiting embodiment of any of the foregoing methods, the method includes shuttling the sutures through the graft while the graft is located outside of the shoulder joint prior to pulling the graft into the shoulder joint.

A method for performing a reconstruction at a rotator cuff according to another exemplary aspect of the present disclosure includes, among other things, exposing an area at a superior glenoid site to improve visibility at the superior glenoid site and preparing bone beds of the superior glenoid site and of a greater tuberosity to expose a bleeding base of bone bed. Two or more suture anchors are placed through a predetermined site in the bone bed of the superior glenoid site. The suture anchors do not penetrate an articular surface. The method includes retrieving at least one suture from inside the joint space, passing the at least one suture through a graft at a location external to the joint space, shuttling the graft into the joint space using a double pulley system, fixating the graft using the at least one suture, and performing a partial closure of the rotator cuff over the top of the graft.

In a further non-limiting embodiment of the foregoing methods, exposing the area at the superior glenoid site comprises performing a posterior interval slide by cutting between a supraspinatus tendon and an infraspinatus tendon to create a gap between the two tendons so as to expand an open work space above the superior glenoid site.

A kit for joint kinematic reconstruction according to another exemplary aspect of the present disclosure includes, among other things, at least (6) suture anchors pre-loaded with a suture tape, at least one dermal allograft and disposable drills, drill guides, punches, and taps for the suture anchors.

In a further non-limiting embodiment of the foregoing method, the method includes an instructional insert with instructive diagrams and a description of a methodology for performing a kinematic reconstruction technique.

In a further non-limiting embodiment of either of the foregoing methods, the at least one dermal graft is pre-threaded with suture.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes surgical techniques for reconstructing an unstable joint. An exemplary surgical technique includes passing a graft into a joint space and securing the graft within the joint space using multiple properly placed sutures. The surgical techniques can be performed to prepare, deliver, and fixate a graft in a relatively fast, anatomically accurate manner that improves joint kinematics.

In some non-limiting embodiments, the surgical techniques include retrieving one or more sutures from inside the joint space, passing the sutures through a graft at a location external to the joint space, shuttling the graft into the joint space, and fixating the graft using the sutures. In other non-limiting embodiments, the graft is sized based on multiple measurements that mark the fixation points of the various sutures. These and other features are described in greater detail in the following paragraphs of this detailed description.

Figure 1:
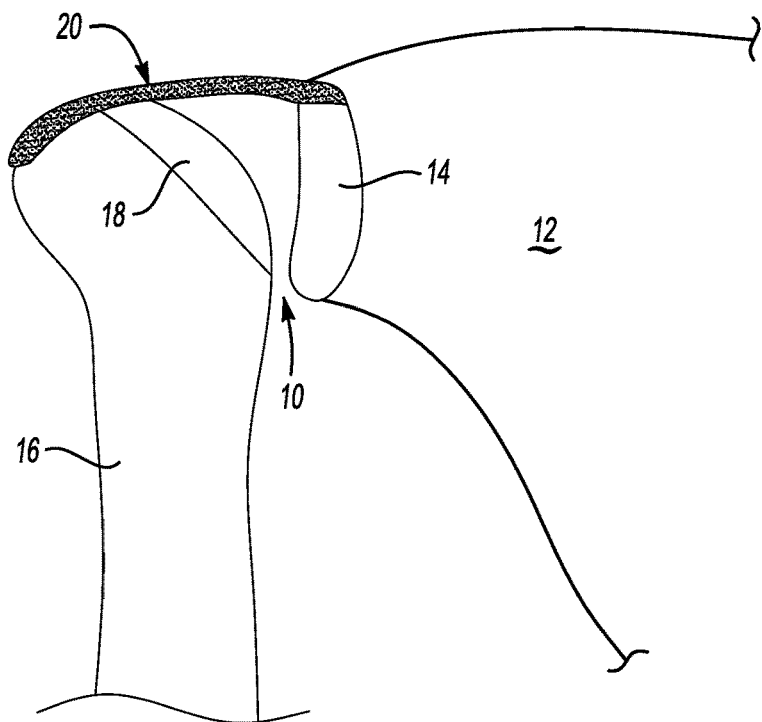
FIG. 1 illustrates a joint of a human musculoskeletal system.

FIG. 1 illustrates a joint 10 of the human musculoskeletal system. The joint 10 may be any joint of the musculoskeletal system of the human body. In one non-limiting embodiment, the joint 10 is the glenohumeral joint of a shoulder. The joint 10 includes multiple bones including a scapula 12 and a humerus 16. Some of these bones articulate relative to one another. For example, the joint 10 includes a ball and socket joint formed between a head 18 of the humerus 16 and a glenoid 14, which is a cup-like recession of the scapula 12 configured to receive the head 18.

A capsule 20 generally covers the joint 10 and is surrounded and reinforced by various muscles, tendons and ligaments that are responsible for keeping the adjoining bones of the joint 10 together. The joint 10 may become unstable if there is significant disruption of the articulating bones (e.g., the humerus 16 and the glenoid 14), the capsule 20, or other surrounding muscles, tendons and/or ligaments. In one non-limiting embodiment, the joint 10 could become unstable in response to a massive irreparable rotator cuff tear.

This disclosure describes joint kinematic reconstruction techniques for reconstructing an unstable joint, such as in response to a massive irreparable rotator cuff tear or other injury. Although joint kinematic reconstruction of a shoulder joint is described throughout this disclosure as one example joint kinematic reconstruction technique, this disclosure is not intended to be limited to shoulder reconstructions. In other words, the various techniques described herein may be employed to reconstruct and/or improve the joint kinematics of any joint of the human musculoskeletal system.

FIGS. 2-8 schematically illustrate an exemplary joint kinematic reconstruction technique. In one non-limiting embodiment, the joint kinematic reconstruction technique is performed as an arthroscopic procedure by working through various arthroscopic portals. However, the exemplary technique could alternatively be performed as an open procedure within the scope of this disclosure. As detailed below, the exemplary joint kinematic reconstruction techniques may be employed to prepare, deliver and fixate a graft within a joint in a manner that improves joint kinematics. The term "joint kinematics" generally refers to the manner in which the bones and surrounding soft tissue of a joint interact with one another during motion.

Figure 2A:
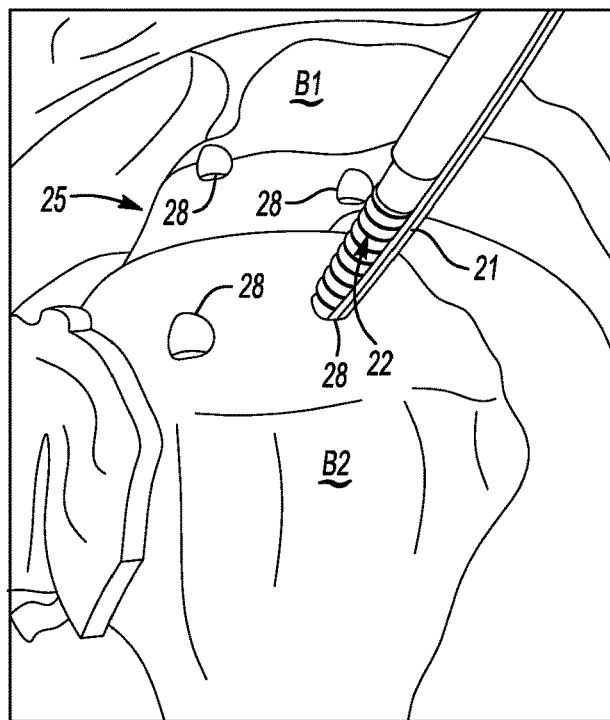
FIGS. 2A and 2B schematically illustrate implantation of suture anchors into articulating bones of an unstable joint.
Figure 2B:
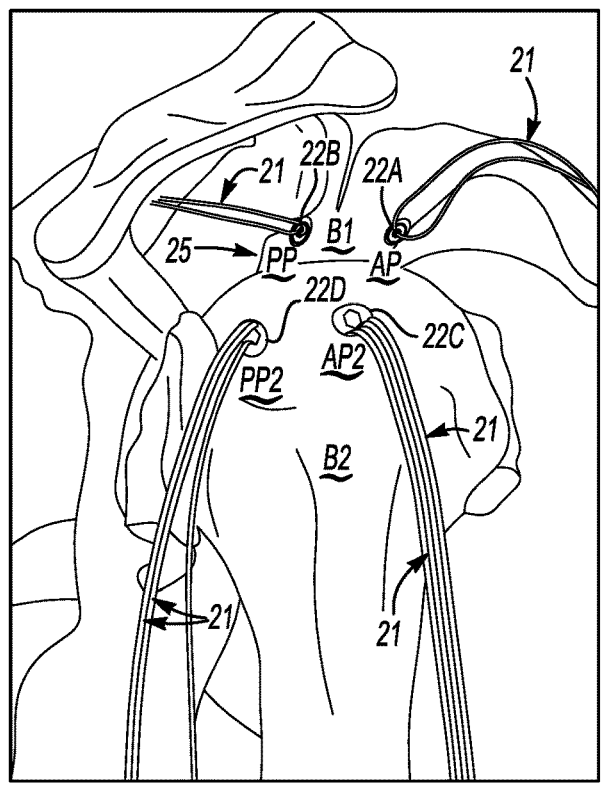
Figure 3A:
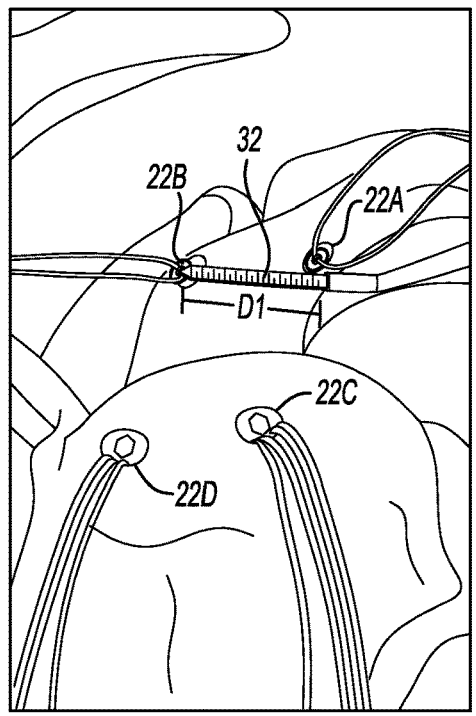
FIGS. 3A, 3B, 3C and 3D schematically illustrate the measurement of various dimensions within a joint space. The measurements are used to size a graft.
Figure 3B:
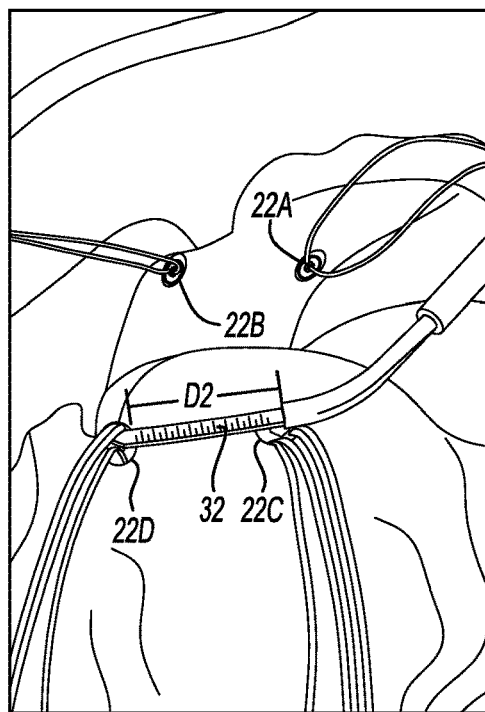
Figure 3C:
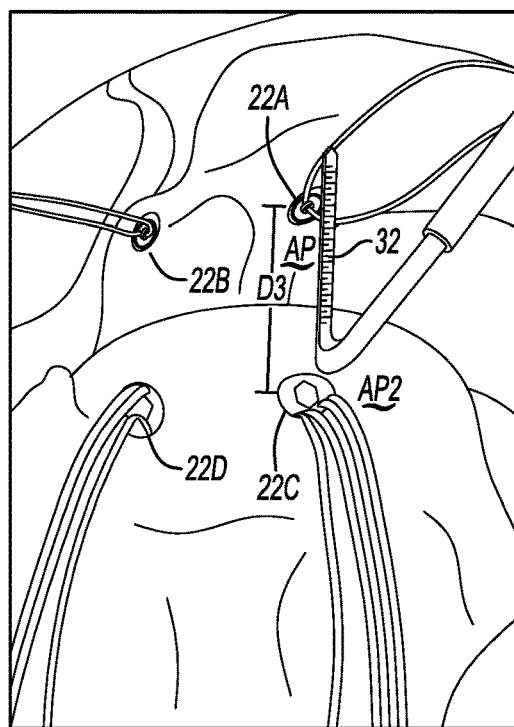
Figure 3D:
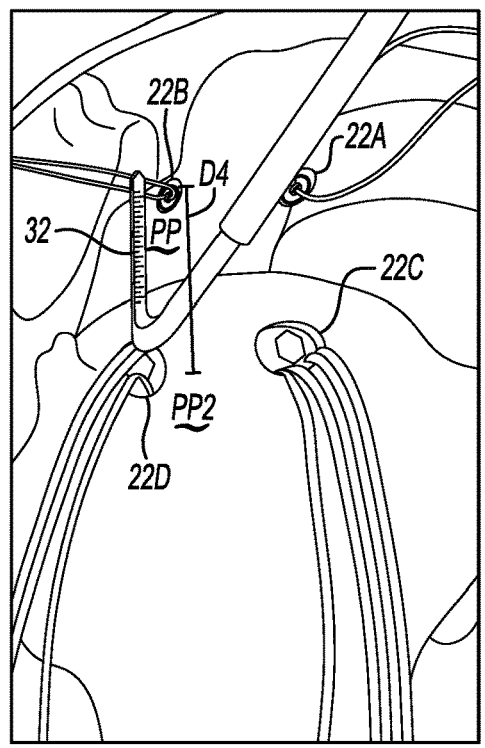

Referring first to FIGS. 2A and 2B, a surgeon may begin the joint kinematic reconstruction technique by selecting a desired positioning for fixating various sutures 21 inside a joint space 25. The fixation locations of the sutures 21 may be selected based on a surgeon's preference and are selected to best restore the joint kinematics of the joint being repaired. The sutures 21 may include individual suture strands, multiple suture strands, suture tape or any other suture-like product.

The sutures 21 may be fixated inside the joint space 25 using various suture anchors 22. Prior to implanting the suture anchors 22, the bone beds of a first bone B1 and a second bone B2 may be prepared for the surgical procedure by debriding, etc. For example, in a non-limiting embodiment where rotator cuff repair is being performed, bone beds of the superior glenoid and greater tuberosity of the humerus can be prepared down to a bleeding base. Electrocautery and/or a motorized shaver may be used to remove soft tissue from the superior glenoid and from the greater tuberosity of the humerus, and a high speed burr may be used to debride the bone to a bleeding base. A ring curette may be used to prepare the articular margin. In preparing the bone surface of the superior glenoid, the superior labrum may become partially detached as a bucket-handle fragment, in which case the torn and unstable portion of the labrum is excised. Since the root of the biceps attaches to the superior labrum in an area that may become unstable as the bone bed is prepared, thereby rendering the biceps root unstable, biceps tenodesis or tenotomy can be performed in cases of superior capsular reconstruction of the shoulder in order to eliminate biceps instability as a potential pain generator. A manual or mechanical pick (e.g., Arthrex's PowerPick™) may be used to create channels (bone vents) between the marrow and the surface of the bone, particularly on the greater tuberosity of the humerus. This procedure serves to enhance access of growth factors and mesenchymal stem cells to the healing interface between the graft and the bone.

Any number of suture anchors 22 may be fixated inside the joint space 25 for attaching the sutures 21, and this disclosure is not limited to the specific number of suture anchors shown in this embodiment. The actual number of suture anchors 22 used is surgery specific and may be quantified as the minimum number of suture anchors that is necessary to achieve graft fixation to the bone or bones of the unstable joint.

Holes 28 may optionally be pre-formed for receiving the suture anchors 22 (see FIG. 2A). Each hole 28 is configured to receive one of the suture anchors 22. A drill, punch, and/or other tools (not shown) may be used to form the holes 28.

In one non-limiting embodiment, shown in FIG. 2B, suture anchors 22A and 22B may be implanted inside the first bone B1 and suture anchors 22C and 22D may be implanted inside the second bone B2, which articulates relative to the first bone B1. The suture anchors 22C, 22D may be similar or different types of suture anchor compared to the suture anchors 22A, 22B. Any type of suture anchors can be used as part of the joint kinematic reconstruction technique.

One or more sutures 21 are connected to each of the suture anchors 22A, 22B, 22C and 22D. Therefore, once the suture anchors 22A, 22B, 22C and 22D have been implanted, the sutures 21 are fixated at desired locations within the joint space 25. In other words, the suture anchors 22A, 22B, 22C and 22D mark the fixation locations of the sutures 21.

In one non-limiting embodiment, the suture anchor 22A is inserted at an interior position AP of the first bone B1 and the suture anchor 22B is inserted at a posterior position PP of the first bone B1. Similarly, the suture anchor 22C may be inserted at an anterior position AP2 position and the suture anchor 22D may be inserted at a posterior position PP2 of the second bone B2. In another non-limiting embodiment, the suture anchors 22A, 22B are implanted into the superior glenoid of the scapula and the suture anchors 22C, 22D are implanted into the articular margin of the greater tuberosity of the humerus. Other locations, however, are also contemplated.

Referring now to FIGS. 3A-3D, a plurality of measurements may be taken in preparation of sizing and preparing a graft, which is shown as feature 30 in FIGS. 4A-4E, for subsequent use to improve the joint kinematics of an unstable joint. A measuring probe 32 may be utilized to take each of measurement. The joint kinematic reconstruction technique may involve sizing the graft based on one or more measurements.

Figure 9:
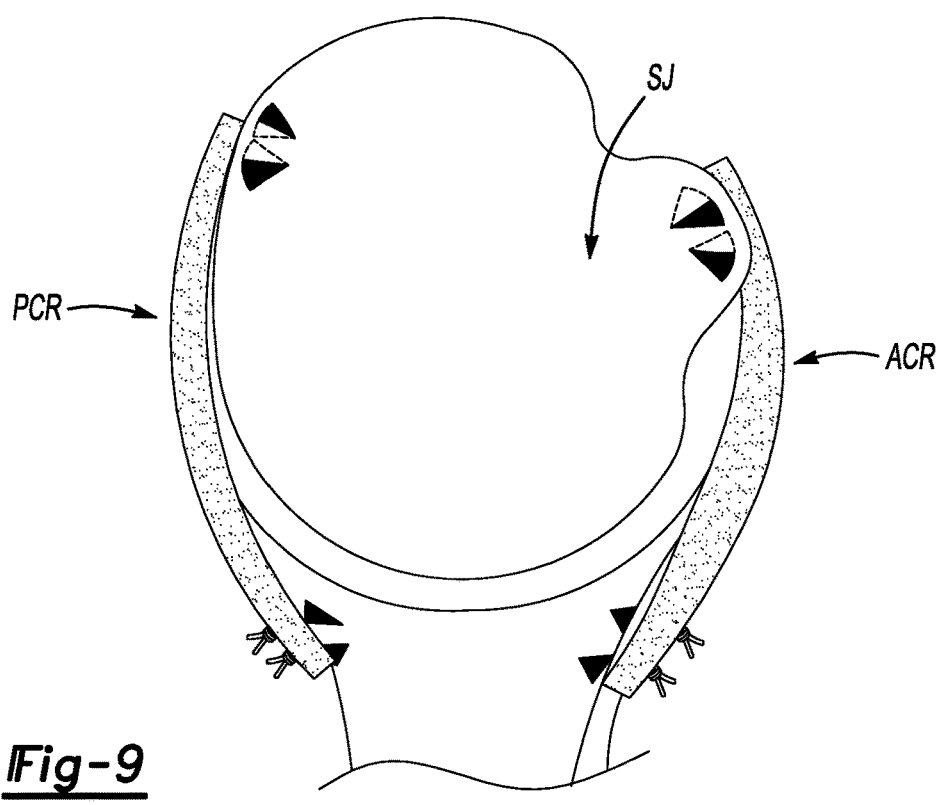
FIG. 9 illustrates additional locations of a joint that can be surgically reconstructed to improve joint kinematics.
Figure 10A:
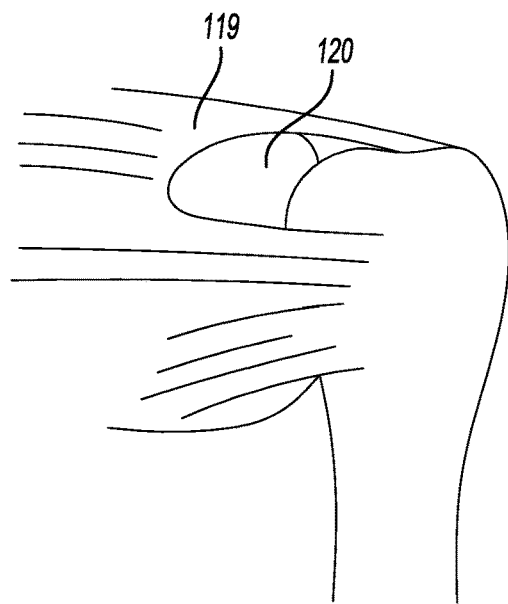
FIGS. 10A, 10B and 10C schematically illustrate exemplary steps for improving superior glenoid visibility, such as by utilizing a posterior interval slide.
Figure 10B:
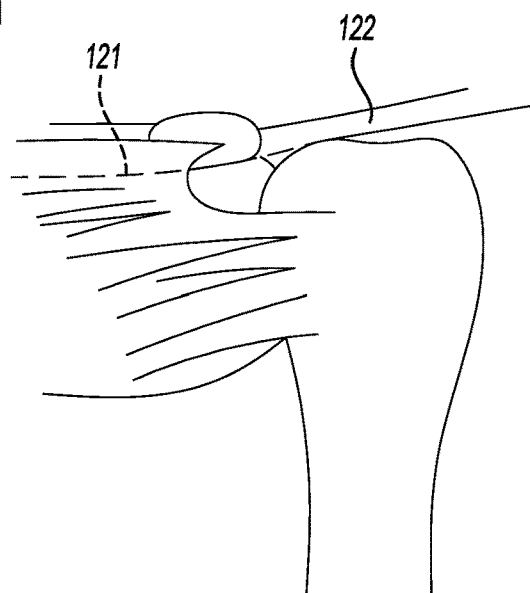
Figure 10C:
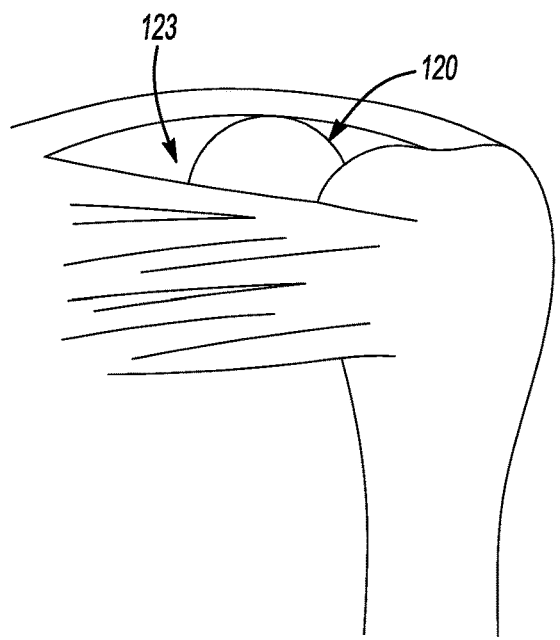

In one non-limiting embodiment, at least four dimensions are measured between the suture anchors 22A-22D for sizing a graft. For example, a first distance D1 may be measured between the suture anchors 22A and 22B (see FIG. 3A), a second distance D2 may be measured between the suture anchors 22C and 22D (see FIG. 3B), a third distance D3 (see FIG. 3C) may be measured between the suture anchors 22A and 22C (i.e., the anchors positioned in the AP and AP2 positions, respectively), and a fourth distance D4 (see FIG. 3D) may be measured between the suture anchors 22B and 22D (i.e., the anchors positioned in the PP and PP2 positions, respectively). In one non-limiting embodiment, the first distance D1 and the second distance D2 are anterior-posterior distances and the third distance D3 and the fourth distance D4 are medial-lateral distances. It should be understood, however, that the directions of these measurements relative to the body could change depending on the type and location of the joint being surgically repaired. For example, in another non-limiting embodiment, the distances D1 and D2 could be superior-inferior distances and the distances D3 and D4 could be medial-lateral distances, such as to perform posterior or anterior capsular reconstruction of a shoulder joint (see, for example, FIG. 9).

FIGS. 4A-4E illustrate the preparation of a graft 30. Once prepared, the graft 30 can be used to reconstruct an unstable joint. The graft 30 could include either an allograft or an autograft. In one non-limiting embodiment, the graft 30 is an acellular dermal extracellular matrix. ArthroFlex®, sold by Arthrex, Inc., is one type of graft suitable for use to perform the exemplary joint kinematic reconstruction techniques of this disclosure.

Figure 4A:
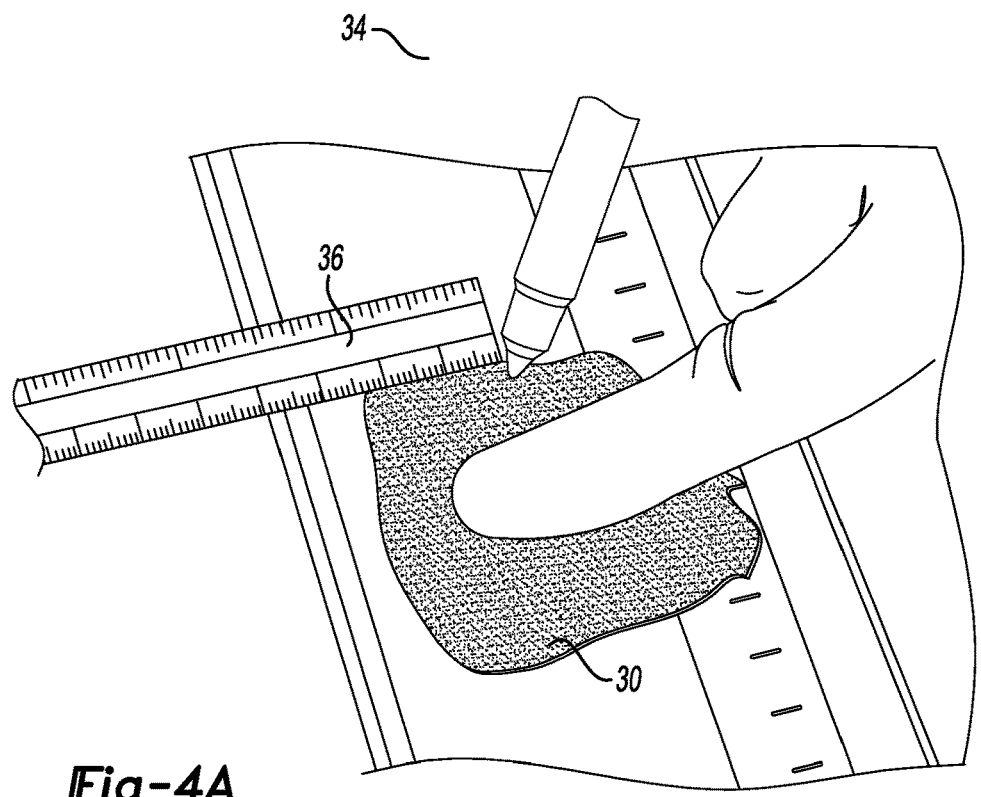
FIGS. 4A, 4B, 4C, 4D and 4E schematically illustrate the preparation of a graft for subsequent use in restoring the joint kinematics of an unstable joint.
Figure 4B:
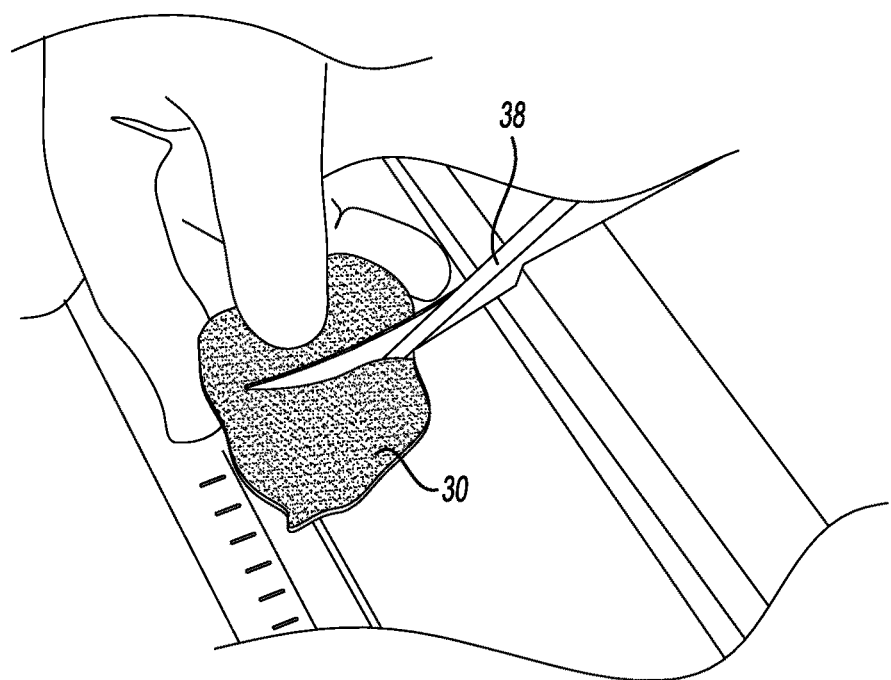

Referring first to FIG. 4A, the graft 30 may be sized using a marking pin 34 and a ruler 36. The graft 30 is sized based on the previously obtained measurements (e.g., distances D1 to D4). In one non-limiting embodiment, at least five to ten millimeters are added around the periphery of the graft 30 to prevent the suture anchors 22 from cutting through the graft 30 after implantation. A cutting device 38, such as scissors or a scalpel, can be used to cut the graft 30 into the desired size and shape (see FIG. 4B).

Figure 4C:
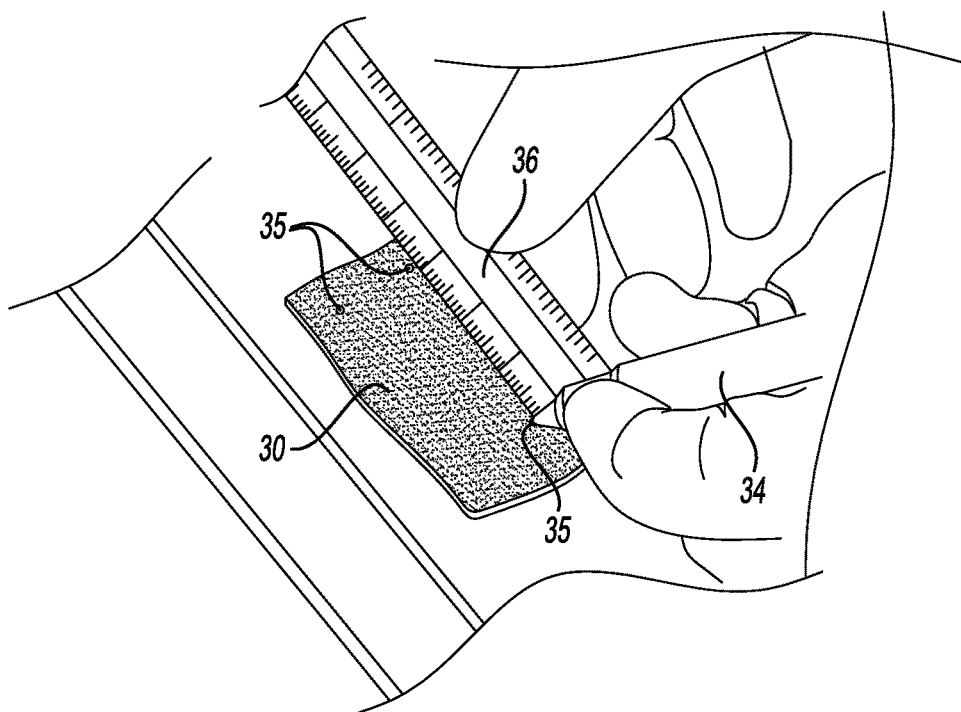
Figure 4D:
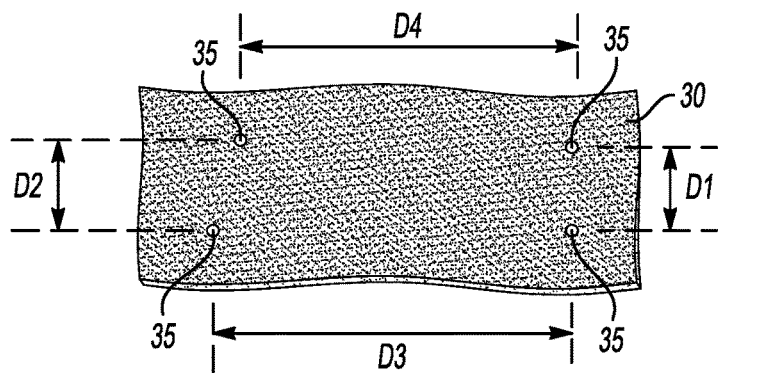

Next, as shown in FIGS. 4C and 4D, a mark 35 is made on the graft 30 to signify the location of each suture anchor 22 and, therefore, the marks 35 designate the location where the sutures 21 will pass through the graft 30. The ruler 36 is used to measure each of the distances D1 to D4 on the graft 30, and the marking pin 34 is used to draw each mark 35.

Figure 4E:
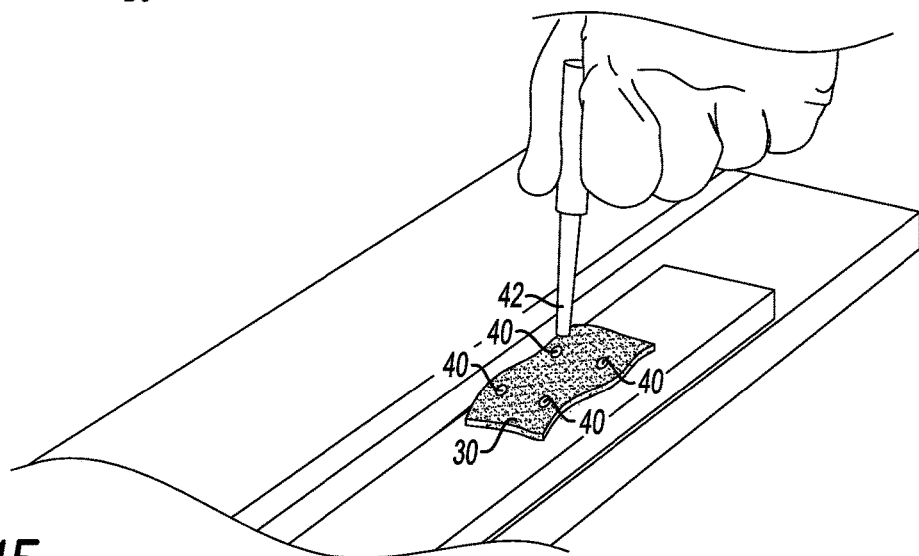

Referring now to FIG. 4E, holes 40 may be punched through the graft 30 at the location of each mark 35. In one non-limiting embodiment, a punch 42 is used to form the holes 40. The holes 40 are oriented and configured to accommodate the sutures 21 that are attached to the implanted suture anchors 22. The holes 40 permit the sutures 21 to slide relative to the graft 30 as the graft 30 is shuttled, pulled, maneuvered or otherwise manipulated into place within a joint space.

Figure 5A:
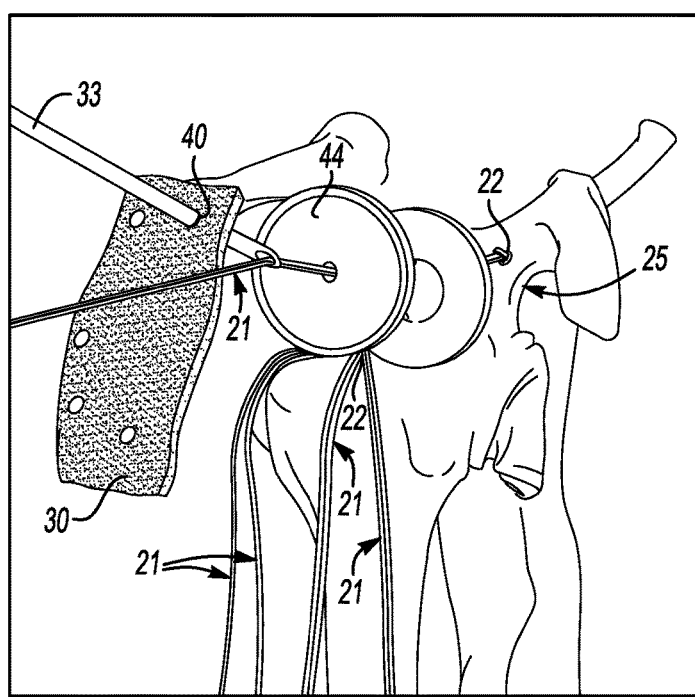
FIGS. 5A and 5B schematically illustrate the retrieval and passage of multiple sutures through a graft.
Figure 5B:
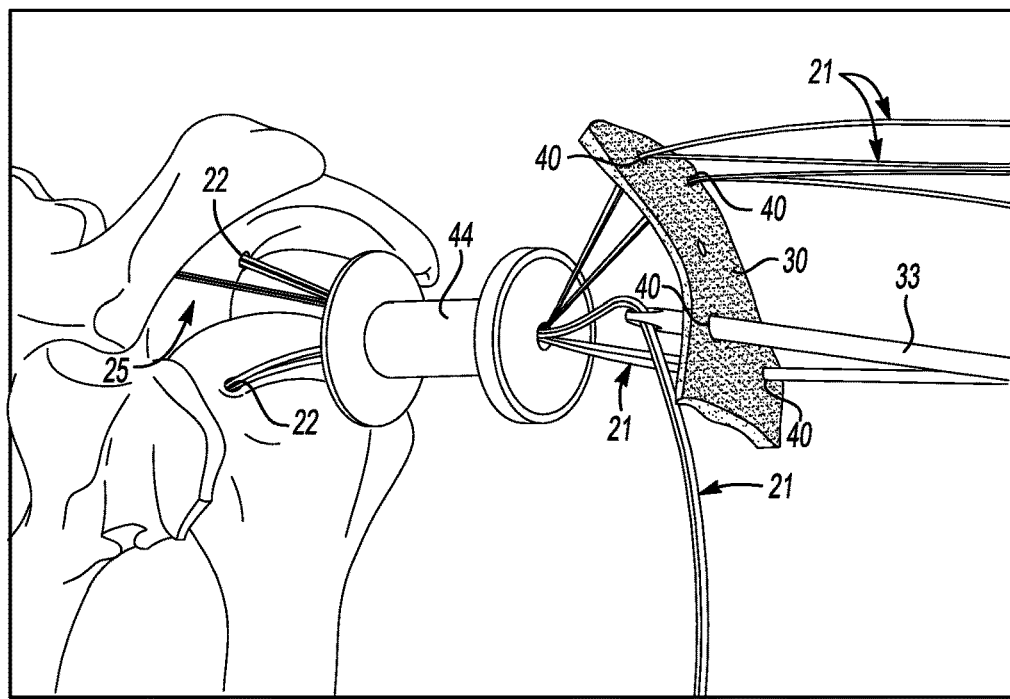
Figure 6A:
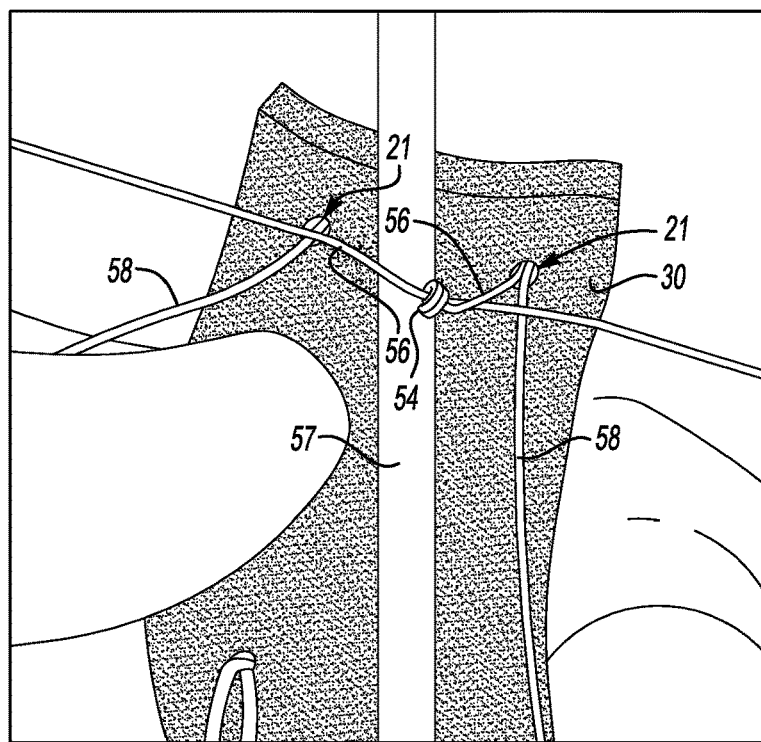
FIGS. 6A, 6B, 6C and 6D schematically illustrate delivery of a graft into a joint space.
Figure 6B:
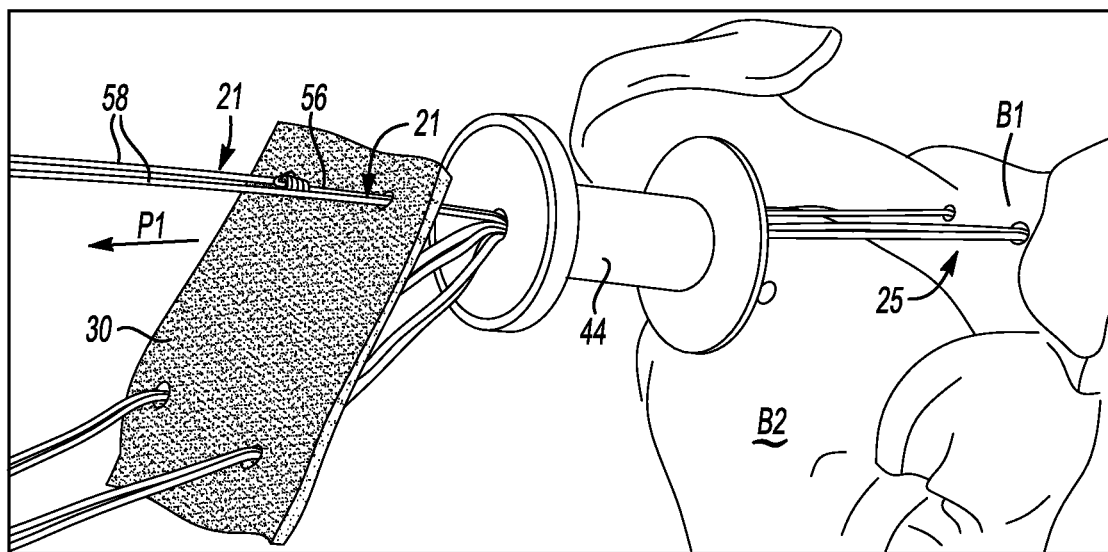
Figure 6C:
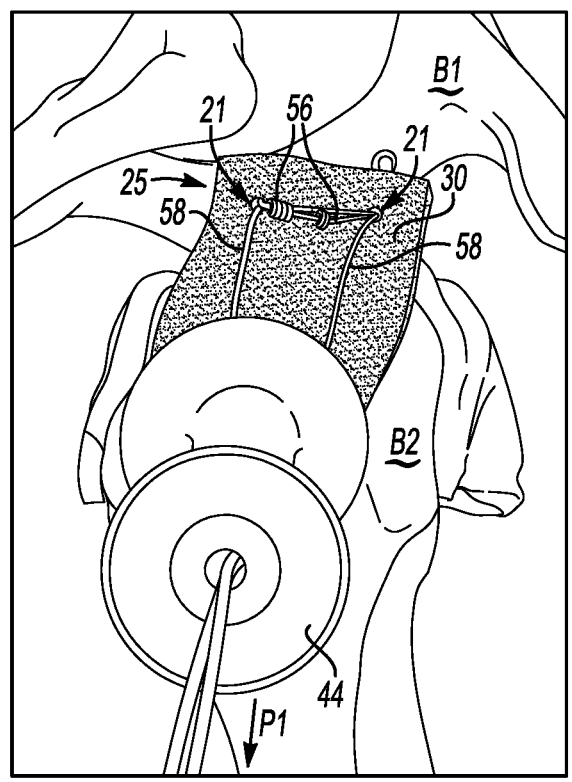
Figure 6D:
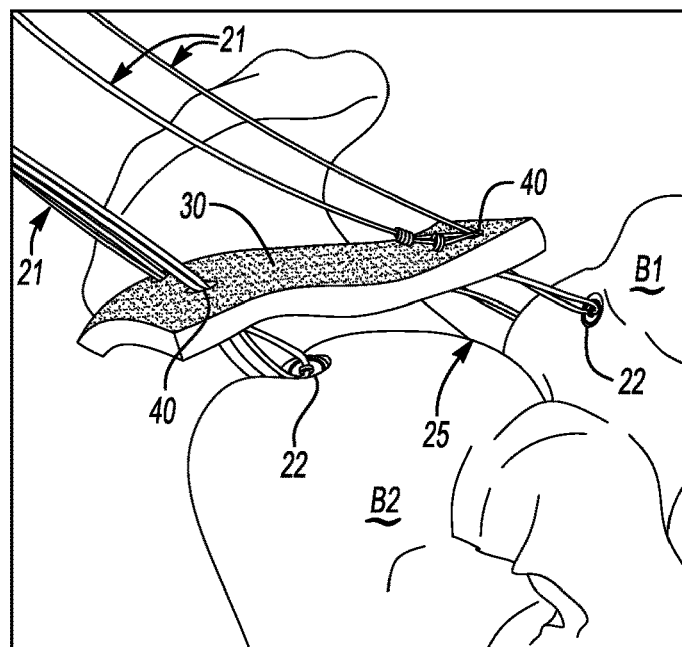

FIGS. 5A and 5B illustrate additional steps of the exemplary joint kinematic reconstruction procedure. The graft 30 is first aligned and oriented at a location external to, or outside of, the joint space 25 in a manner that mimics its implanted position. Sutures 21, which have already been fixated inside the joint space 25, may then be retrieved from each implanted suture anchor 22. A suture passer 33 and/or other surgical instruments can be used to retrieve and pass each suture 21. In one non-limiting embodiment, the sutures 21 are pulled outwardly through a cannula 44 and then inserted through the graft 30 while the graft 30 is located outside of the joint space 25. In another non-limiting embodiment, the sutures 21 are retrieved from the joint space 25 one-by-one (i.e., sequentially), passed through the appropriate hole 40 of the graft 30, and then tensioned prior to shuttling an additional suture 21 through the cannula 44. Shuttling the sutures 21 individually in this manner helps prevent tangling of the sutures 21. Each hole 40 of the graft 30 is configured to accommodate one or more of the sutures 21.

Referring now to FIGS. 6A-6D, the graft 30 is next shuttled into the joint space 25. The graft 30 may be shuttled through the cannula 44 if performing an arthroscopic procedure. A person of ordinary skill in the art would be able to position the various arthroscopic portals required for performing an arthroscopic procedure. In one non-limiting embodiment, the graft 30 is partially folded to ease insertion through the cannula 44.

In another non-limiting embodiment, the graft 30 is advanced into the joint space 25 using a pulley technique. For example, an individual suture limb 56 from each suture 21 that has been fixated to the first bone B1 may be tied together over a rigid instrument 57 (see FIG. 6A). These suture limbs 56 that extend beyond knot 54 may then be cut from the tied sutures 21. Additional suture limbs 58 from the sutures 21 of the first bone B1 may then be pulled in a direction P1 to begin to shuttle the graft 30 down into the joint space 25 (see FIGS. 6B and 6C). In one non-limiting embodiment, each of the suture limbs 58 may be toggled back and forth to move the graft 30 into the joint space 25. Once the graft 30 is through the cannula 44 and inside the joint space 25, the sutures 21 can be further tensioned to position the graft 30 as desired relative to the first bone B1 and the second bone B2 (see FIG. 6D). When properly positioned, each hole 40 of the graft 30 is aligned over top of the suture anchor 22 from which the suture 21 that is received through that particular hole 40 extends. The pulley technique described above can be used at the medial side of the graft 30, the lateral side of the graft 30, or both, to advance the graft 30 into the joint space 25.

Figure 7A:
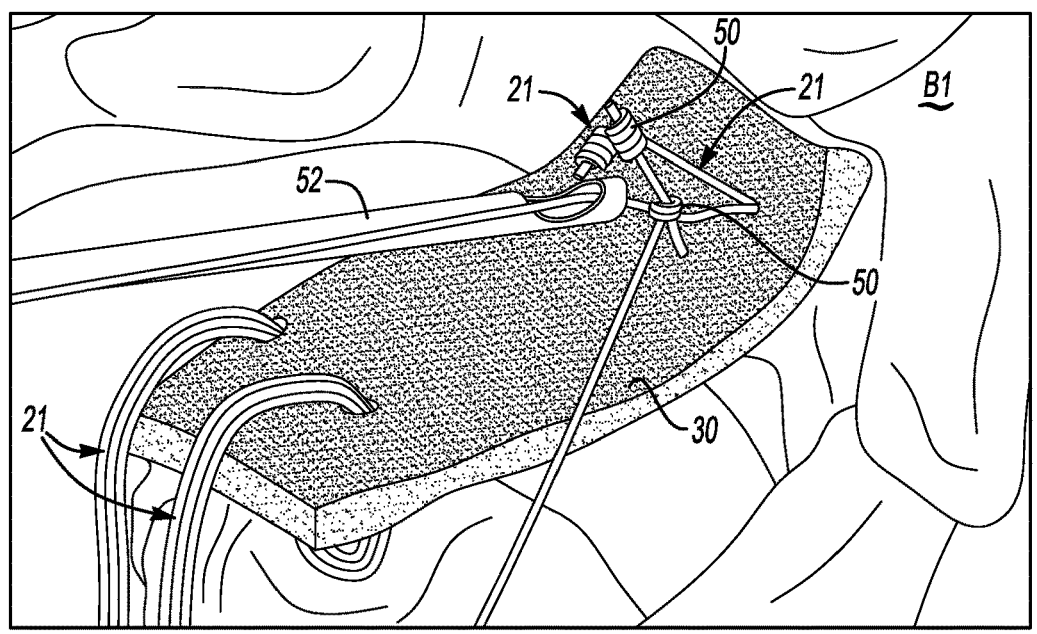
FIGS. 7A and 7B schematically illustrate exemplary fixation methods for securing a graft to a first bone of the joint.
Figure 7B:
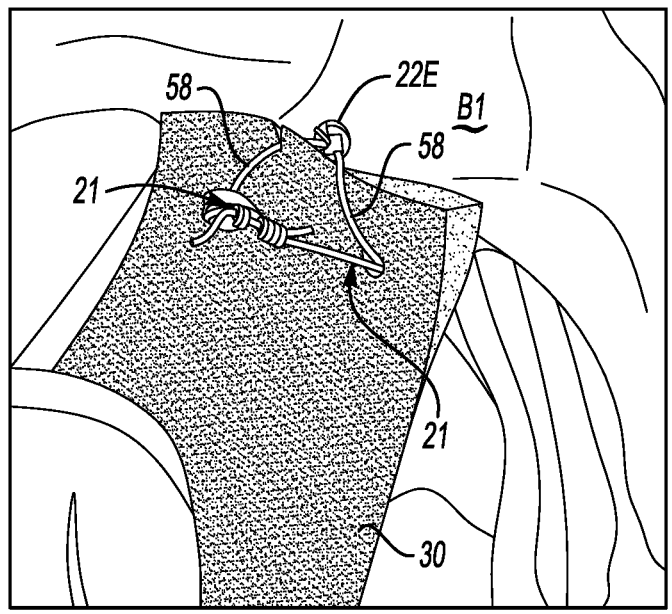

The graft 30 may next be fixated into place using the various sutures 21. A variety of fixation methods can be utilized to achieve fixation of the graft 30. FIGS. 7A and 7B illustrate exemplary techniques for fixating the graft 30 to the first bone B1. Referring first to FIG. 7A, the sutures 21 from suture anchors 22A and 22B (suture anchors covered by the graft 30 in these figures), which have already been fixated inside the first bone B1, may be used to tie multiple knots 50 over the graft 30. Various surgical tools, such as a knot pusher 52, may be used to tie the knots 50 over the graft 30 to achieve fixation to the first bone B1.

Alternatively, as shown in FIG. 7B, an additional suture anchor 22E may be inserted into the first bone B1 at a location adjacent (medial in this example) to the graft 30. In one non-limiting embodiment, the suture anchor 22E is a knotless suture anchor that is configured to receive suture limbs 58 of the sutures 21, which extend from suture anchors 22A and 22B, for knotlessly fixating the graft 30 to the first bone B1. This may be referred to as a knotless bridge technique.

Figure 8A:
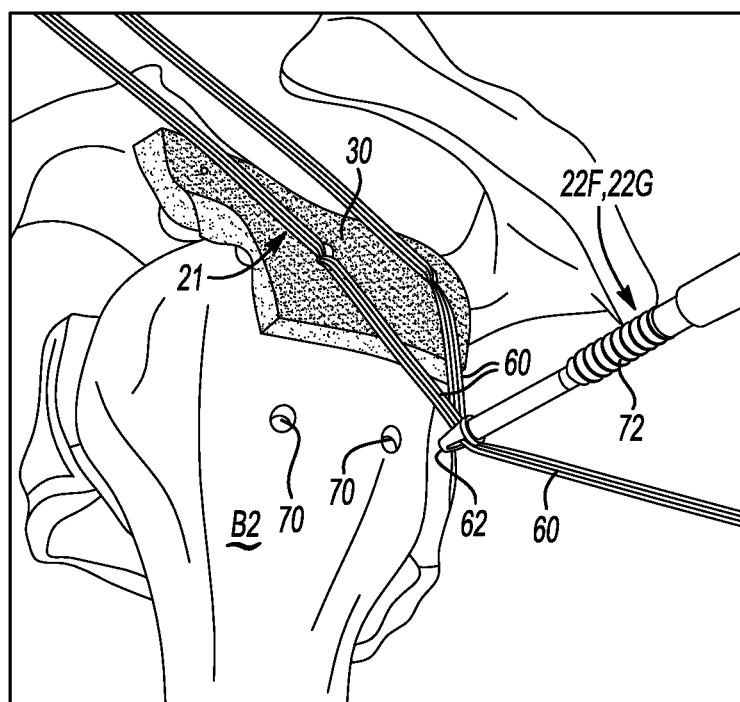
FIGS. 8A and 8B schematically illustrate exemplary fixation methods for securing a graft to a second bone of the joint.
Figure 8B:
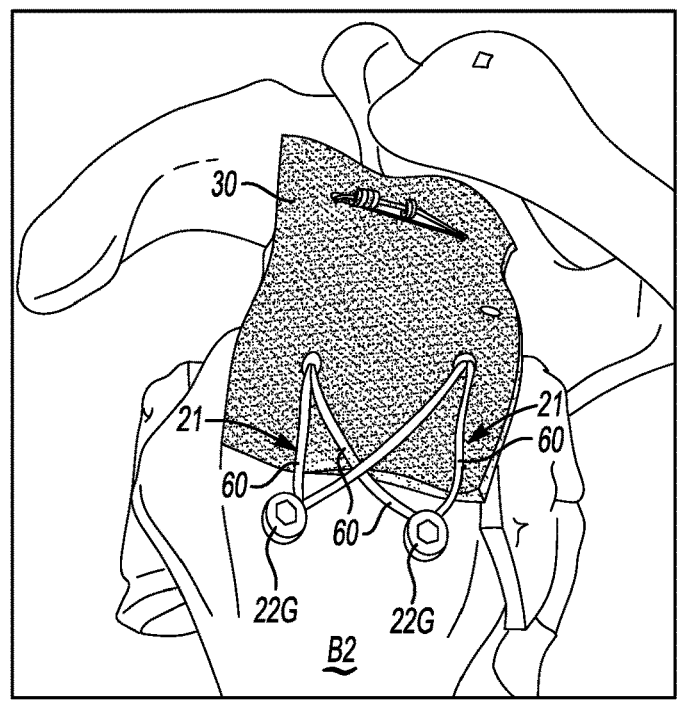

FIGS. 8A and 8B illustrate an exemplary technique for fixating the graft 30 to the second bone B2. For example, additional suture anchors 22F and 22G may be inserted into the second bone B2 at a location adjacent (lateral in this example) to the graft 30. Holes 70 may optionally be pre-formed into the second bone B2 for receiving the suture anchors 22F, 22G. Suture limbs 60 from the sutures 21 that are attached to the suture anchors 22C, 22D (covered by graft 30 in these figures) may be passed through an eyelet 62 of each suture anchor 22F, 22G. The suture anchors 22F, 22G may then be inserted into the holes 70. An anchor body 72 of each suture anchor 22F, 22G may be moved toward the eyelet 62 to trap the suture limbs 60 between the second bone B2 and the anchor body 72 to knotlessly fixate the graft 30 to the second bone B2. Although not shown, various back-up stitches may optionally be added around the periphery of the graft 30 to augment fixation.

Alternatively, sutures 21 may be passed through the lateral part of the graft 30 arthroscopically with a suture passer (e.g., Arthrex's FastPass Scorpion™) after the graft 30 has been shuttled into the shoulder. The graft 30 may be fixed either by knotted double row techniques which may be either bridging (linked double-row) or non-bridging (non-linked double-row), or it may be fixed by single-row knotted or knotless techniques. After the graft 30 has been secured, medial vascularized tissue may optionally be incorporated into the repair. For example, the suture limbs from the superior glenoid anchors can be left long after securing the graft 30, and then the tails can be used to suture viable tissues from the adjacent rotator cuff into the graft 30, thereby encouraging vascularization of the graft 30. If portions of the rotator cuff can be repaired over the top of the graft 30 by means of margin convergence side-to-side sutures, then a partial repair of those cuff tissues can be performed, even after a posterior interval slide has been performed. If tendon-to-bone repair of the posterior rotator cuff was performed prior to placing the graft 30, then a side-to-side repair of the posterior cuff to the graft 30 can be performed. Anteriorly, if there is robust rotator interval tissue adjacent to the anterior margin of the graft 30, it can be sutured to the graft 30 in side-to-side fashion. If there is no rotator interval tissue remaining, then the anterior margin of the graft 30 may be left as an unsecured free margin.

Candidates for a superior capsular reconstruction are typically in one of two categories of massive irreparable rotator cuff tears: 1) those with pseudoparalysis; and 2) those with proximal migration of the humerus allowing creation of a painful acromiohumeral articulation.

Occasionally a patient may have a combination of irreparable rotator cuff tear with proximal humeral migration and/or pseudoparalysis in association with significant degenerative arthritis of the shoulder, yet not be a candidate for shoulder arthroplasty either because of young age, high activity level, or both. In such patients, one might perform a dual grafting procedure, using one graft for a superior capsular reconstruction and another graft (e.g. Arthroflex® dermal allograft) for resurfacing the degenerative glenoid in order to re-establish the pad between the glenoid and the humeral head that has been lost by degeneration of the articular cartilage. In such cases, a capsular release of the anterior, posterior and inferior capsules can first be performed. Then, the glenoid resurfacing is done by introducing and fixing the graft to knotted or knotless anchors around the periphery of the glenoid. Once the resurfacing graft has been fixed in place, the superior capsular reconstruction is performed with a graft. In some cases, the same anchors in the superior glenoid might be used to help secure both grafts, while in other cases separate sets of anchors in the superior glenoid might be needed for each graft.

In one non-limiting implementation of the surgical technique described above and illustrated in FIGS. 2A-8B, the joint kinematic reconstruction technique is utilized to perform a superior capsular reconstruction of a shoulder joint. However, other reconstructions can also be performed, including but not limited to a posterior capsular reconstruction PCR or anterior capsular reconstruction ACR of a shoulder joint SJ (shown schematically in FIG. 9). Similar techniques can also be performed to improve joint kinematics in other unstable joints of the human musculoskeletal system.

Augmentation of biologic tissues used in anterior capsular reconstructions ACR and posterior capsular reconstructions PCR may also be performed utilizing the surgical techniques described herein (e.g., augmentation of an anterior split subscapularis tendon flap that is done in the case of capsular insufficiency). Anterior capsular reconstruction ACR may also be performed along with a Latarjet reconstruction (coracoid bone graft), particularly if the subscapularis muscle-tendon unit has been significantly damaged. Similar techniques can also be performed to improve joint kinematics in other unstable joints of the human musculoskeletal system. In addition, any tissue that was cut can then be repaired or partially repaired as much as possible, such as by suture.

FIGS. 10-19 schematically illustrate another exemplary joint kinematic reconstruction technique. FIGS. 10A-10C illustrate a first step of a superior capsular reconstruction method. Surgically exposing the superior glenoid 120 may be needed where visibility of the superior glenoid 120 needs to be improved, such as, for example, where visibility of the superior glenoid 120 is obscured by an overlying rotator cuff 119 (see, for example, FIG. 10A). After determining that a rotator cuff tear is irreparable, and where exposure of the superior glenoid 120 needs to be improved, a posterior interval slide may be provided by cutting between the supraspinature and infraspinature along cut line 121 using an appropriate surgical cutting device, such as arthroscopic scissors 122 (see, for example, FIG. 10B). As illustrated in FIG. 10C, the superior glenoid 120 then becomes well exposed (as shown schematically at reference numeral 123), thus providing for improved access and easier insertion of suture anchors during the repair.

A second step of the joint kinematic reconstruction technique may include preparing the bone beds down to a bleeding base (superior glenoid and greater tuberosity of humerus) with ring curettes or other tools.

Figure 11A:
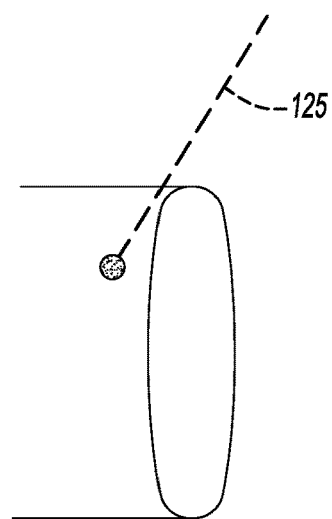
FIG. 11A schematically illustrates a proper trajectory of a suture anchor placement.
Figure 11B:
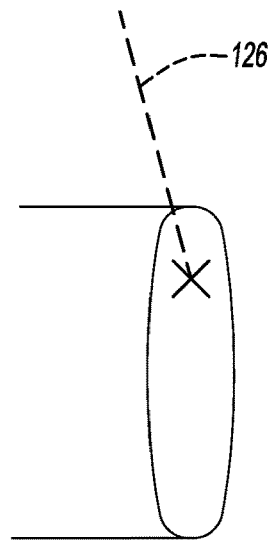
FIG. 11B illustrates an improper trajectory of a suture anchor placement.

FIG. 11A illustrates the proper placement of superior glenoid anchors so as to assure a proper trajectory. Placement of the superior glenoid anchors should be angled with a small degree of lateral—to medial trajectory in order to avoid penetration of the articular surface, which could compromise the result by predisposing toward the development of degenerative arthritis. As illustrated, the proper placement through a portal permits a proper angle of approach along a trajectory line 125. This placement assures that the anchor is fully in the bone and does not penetrate the articular surface. An improper placement of anchors, and resulting improper trajectory line 126, is schematically illustrated in FIG. 11B.

Figure 12A:
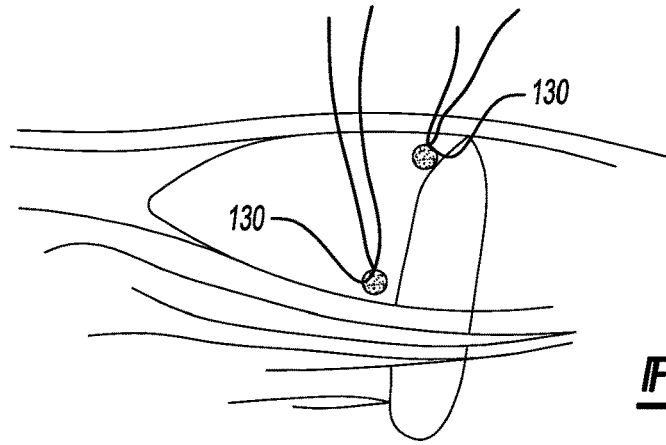
FIG. 12A illustrates suture anchor placement in a superior glenoid.
Figure 12B:
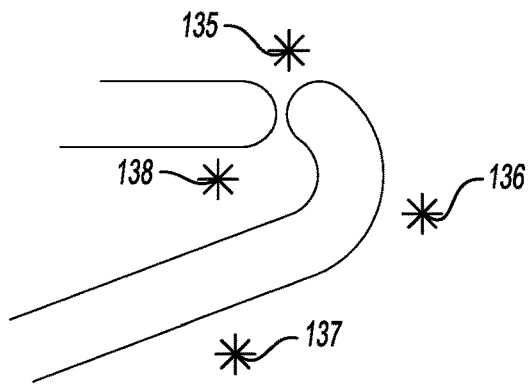
FIG. 12B schematically illustrates portals through which superior glenoid suture anchors may be placed.

FIGS. 12A and 12B illustrate placement of glenoid anchors 130 as part of the joint kinematic reconstruction technique. As illustrated in FIG. 12A, (2) glenoid anchors 130 are placed anterior to the supraglenoid tubercle (origin of long head of biceps; posterior anchor placed at posterior aspect of tendon defect). FIG. 12B illustrates various portal options for placement of anchors, including an anterosuperior portal 135, a modified Neviasen portal 138, a Port of Wilmington 136 or a posterior scapular spine portal 137.

In an embodiment, a suture or other flexible material may be passed through residual cuff tissue and retrieved out of the Neviasen portal 138 as a retention suture to hold the native rotator cuff tissue out of the way for better visualizing the superior glenoid to debride the area, attach anchors, and set the graft down under the rotator cuff. This will allow for superior capsule reconstruction with rotator cuff to follow the reconstruction without harming the native tissue by cutting or resecting it.

Figure 13:
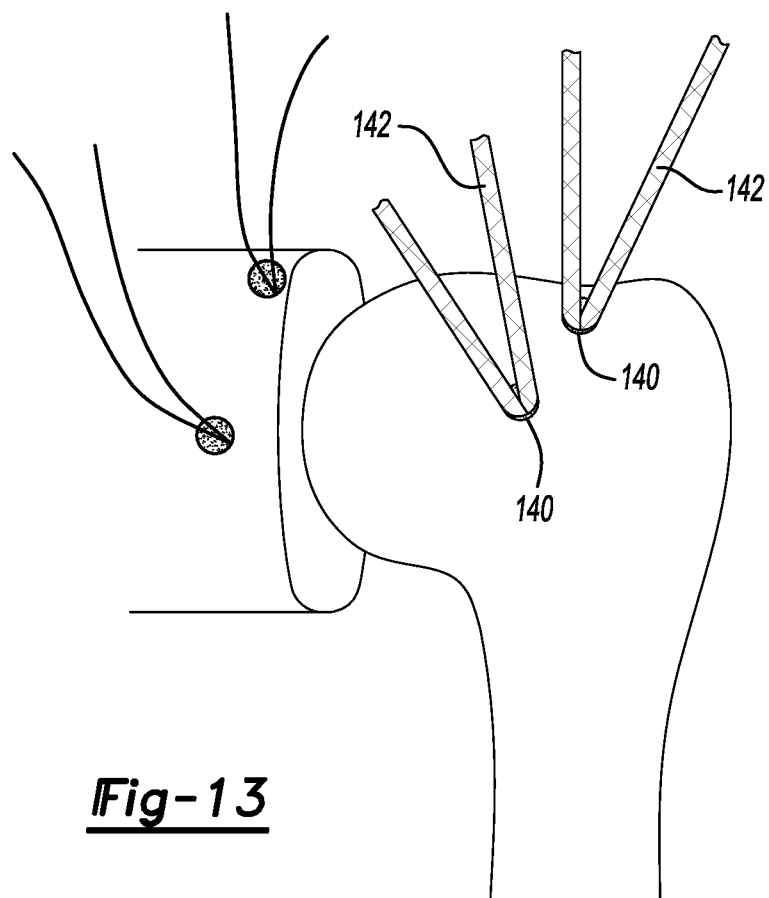
FIG. 13 illustrates anchor placement at the articular margin of the humerus.

FIG. 13 illustrates placement of anchors 140 in the humerus. Two or more anchors 140 may be pre-placed at the articular margin of the humerus, in one non-limiting embodiment. The anchors 140 may be preloaded with suture tape 142.

Figure 14:
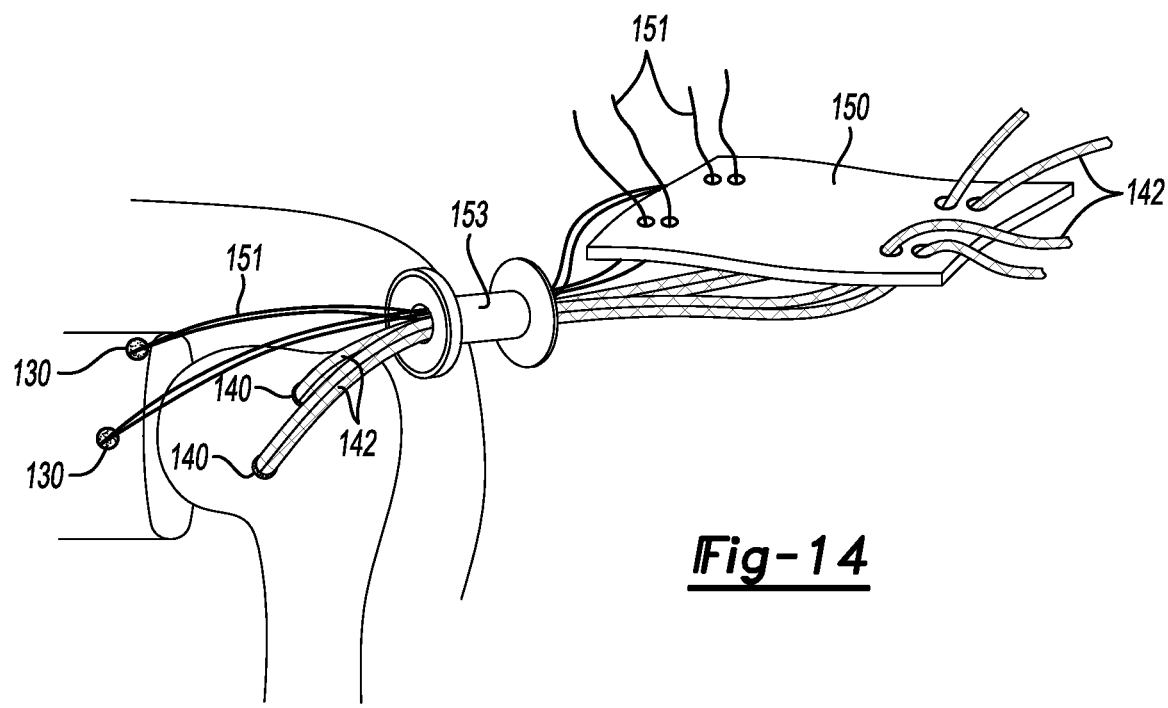
FIG. 14 illustrates the arrangement and pattern of sutures as they are pulled through a lateral cannula.

FIG. 14 illustrates yet another step of the joint kinematic reconstruction technique. In this step, the size of the defect is measured and marks are prepared on a graft 150 to identify the sites at which suture 151 or suture tape 142 is to be passed. By way of example, the defect may be measured with a calibrated probe (with the shoulder being positioned in 20° abduction) and a distance determined and recorded. The distances between all sutures 151 or suture tape 142 should also be measured between all suture anchors 130, 140. The graft 150 should be extended to approximately 5 mm beyond the suture anchors 130 in each case, and the graft 150 should extend 10 to 12 mm lateral to the humeral head anchors 140 (so as to cover the normal footprint of the rotator cuff). All of the sutures 151 should then be pulled through a lateral cannula 153, keeping relative orientation of the sutures 151 the same as it is in the joint. The sutures 151 should then be placed through the corresponding marks on the graft 150.

Figure 15:
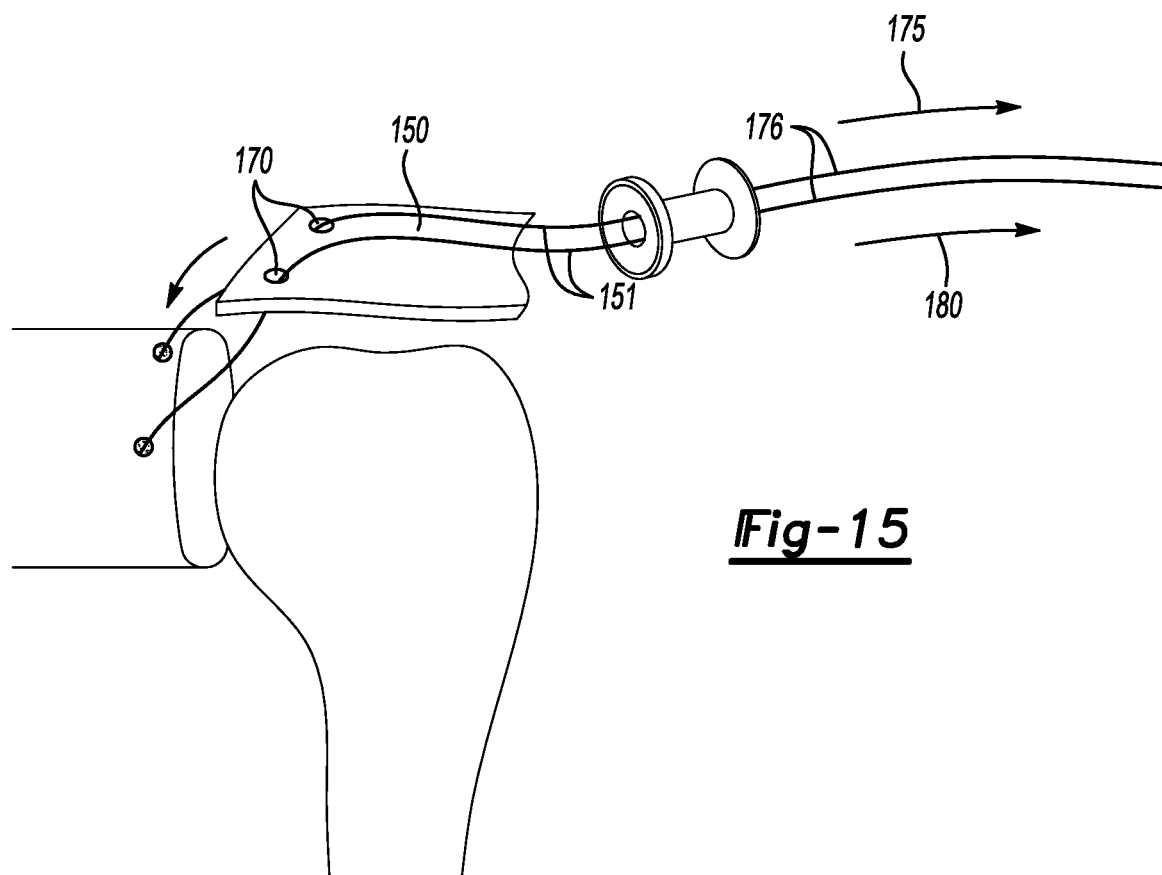
FIG. 15 illustrates the utilization of a double pulley technique as part of a joint kinematic reconstructive technique.
Figure 16:
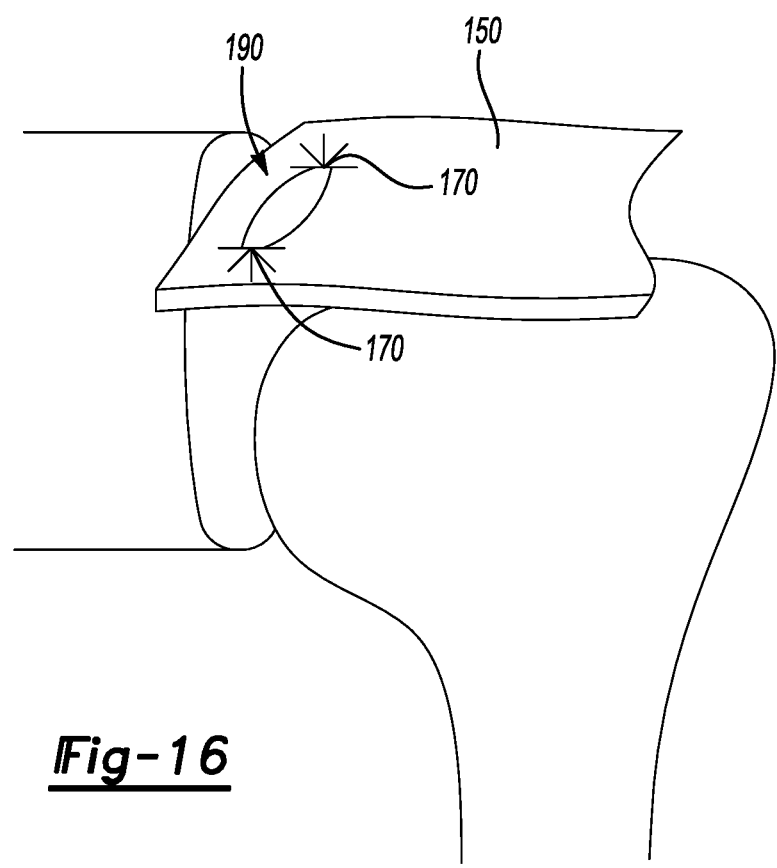
FIG. 16 illustrates securing a graft to the glenoid using a double mattress knot configuration.

FIG. 15 schematically illustrates shuttling the graft 150 into the joint. Mulberry knots 170 are tied on one limb of each suture pair 151 from the glenoid. By reciprocally pulling (in the direction of arrows 175, 180) on free suture limbs 176 that are opposite the knotted limbs, the graft 150 is easily shuttled into the shoulder and over top of the superior glenoid anchors. Next, as shown in FIG. 16, the graft 150 can be secured to the glenoid by tying the glenoid sutures medially as a double mattress knot configuration 190. For example, the suture limbs that have the mulberry knots 170 can be sutured together, followed by removing the slack from the suture pairs by pulling on the free limbs of those two suture pairs, and then tying the two free suture limbs together to complete the double mattress suture configuration 190.

Figure 17:
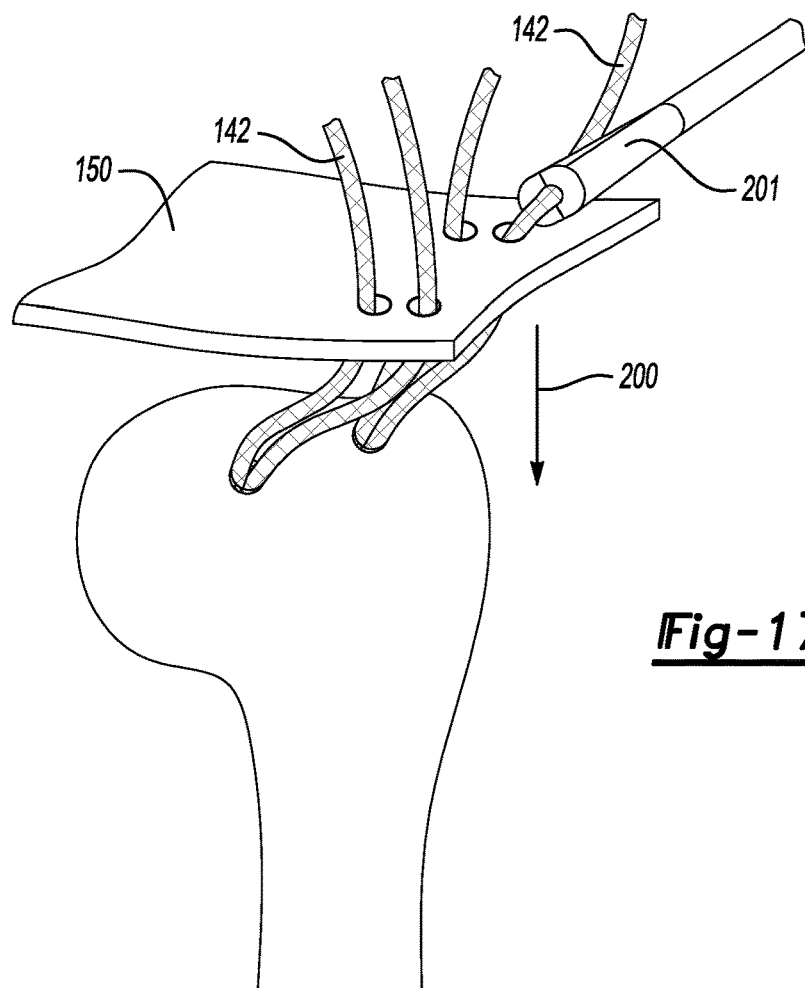
FIG. 17 illustrates pushing a lateral part of a graft down onto the humerus.
Figure 18:
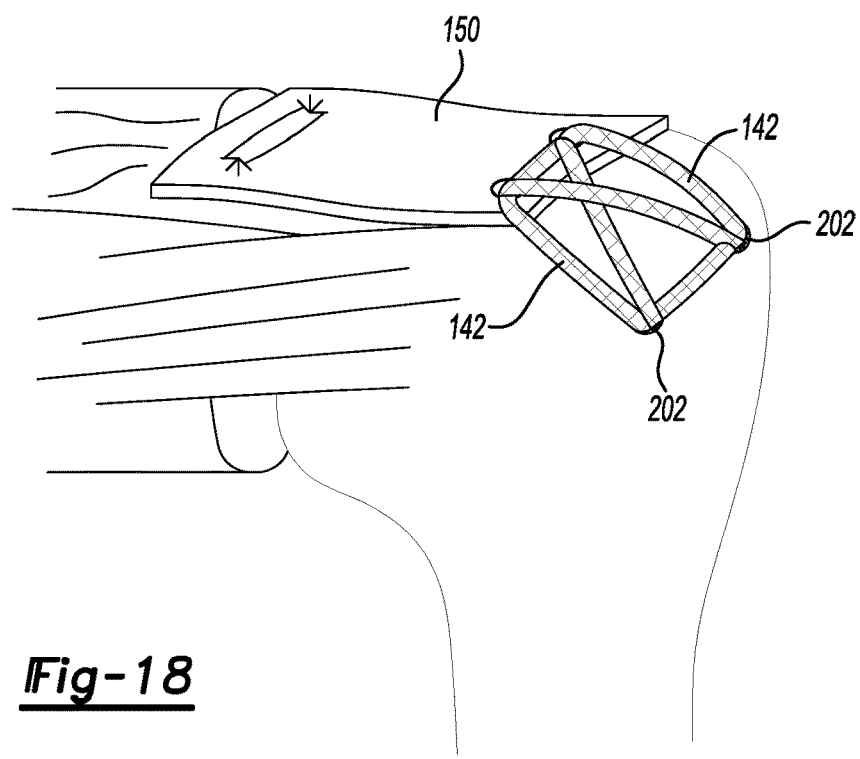
FIG. 18 illustrates a fully-seated graft.

Referring now to FIG. 17, the lateral part of the graft 150 may be pushed down in the direction of arrow 200 over the suture tape 142. A tool 201, such as a tensioner/retriever, may be used to push the graft 150 down. Once the graft 150 is fully seated, and all slack has been taken out of the suture tape 142, the suture tape 142 can be crisscrossed and fixed to two (2) lateral suture anchors 202 in a bridging configuration (see FIG. 18).

Figure 19:
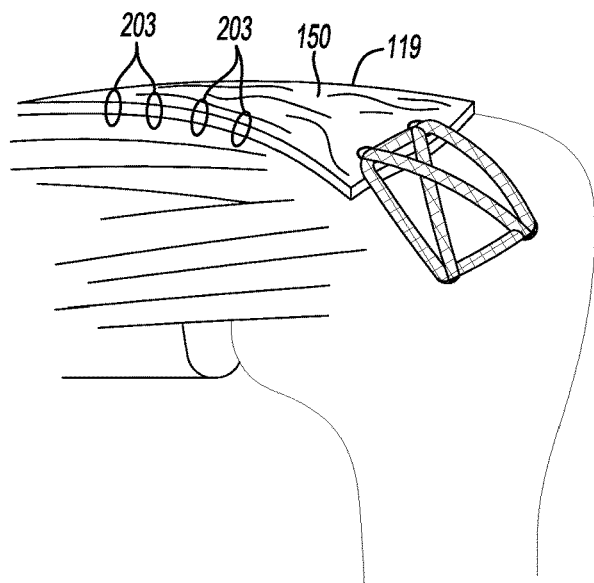
FIG. 19 illustrates a partial closure/repair of a rotator cuff over top of a graft using side-to-side margin convergence sutures.

FIG. 19 illustrates an additional step that may be taken in completion of the exemplary reconstruction procedure, wherein a partial or complete closure/repair of the rotator cuff 119 over the top of the graft 150 is performed. In one non-limiting embodiment, the step is accomplished by creating side-to-side margin convergence sutures 203 over the top of the graft 150. After the completion of the side-to-side margin convergence sutures 203, the graft 150 may remain visible through the residual defect in the rotator cuff 119.

Figure 20A:
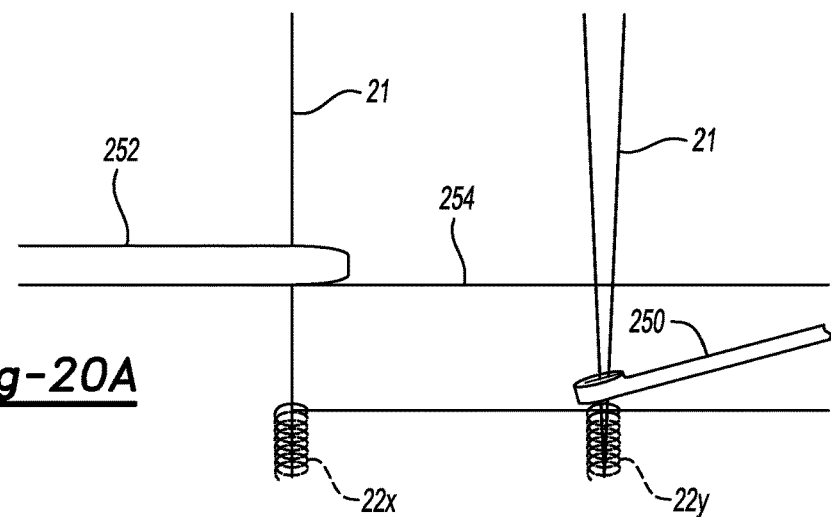
FIGS. 20A and 20B illustrate placements of suture anchors within a joint.
Figure 20B:
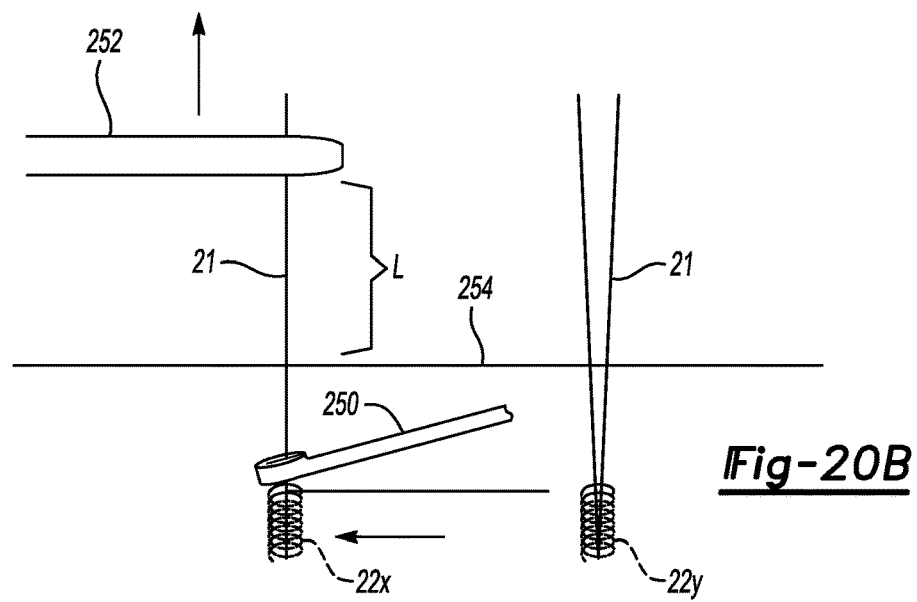

An alternative way of sizing the graft and measuring between suture anchors 22X, 22Y is shown in FIGS. 20A and 20B. With this method, a suture 21 that extends from the suture anchor 22Y may be grasped with an arthroscopic grasper 250. A hemostat 252 may be clamped to that same suture limb 21 at skin surface 254 where the suture 21 exits the body. Then, the hemostat 252 and the grasper 250 simultaneously pull the suture limb 21 until the grasper 250 that is inside the shoulder is positioned over the suture anchor 22X, whose distance from the suture anchor 22Y is being measured. Then, all the slack is taken out of the suture limb 21 by maintaining the position of the suture 21 and grasper 250 over the top of the suture anchor 22X while the external hemostat 252 tightens the suture limb 21 externally (see FIG. 20B), thereby removing the slack. The length L of the suture 21 between the hemostat 252 and the surface of the skin 254 is then measured. The distance between the hemostat 252 and the skin 254 should be equal to the distance between the suture anchors 22X, 22Y.

Figure 21A:
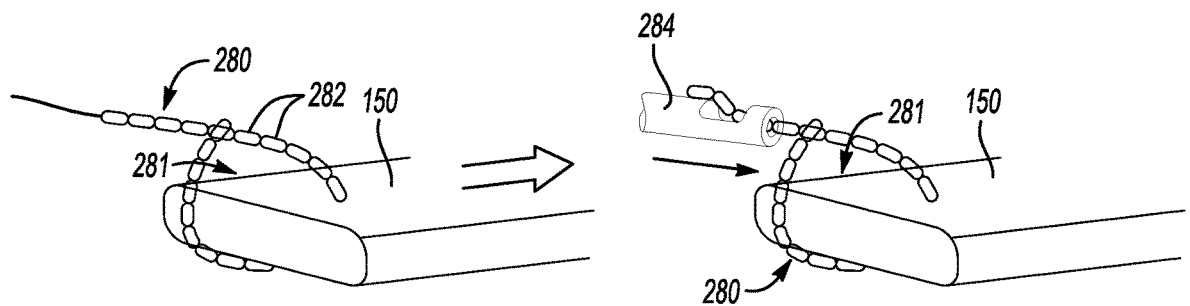
FIG. 21A illustrates a single row suture technique.
Figure 21B:
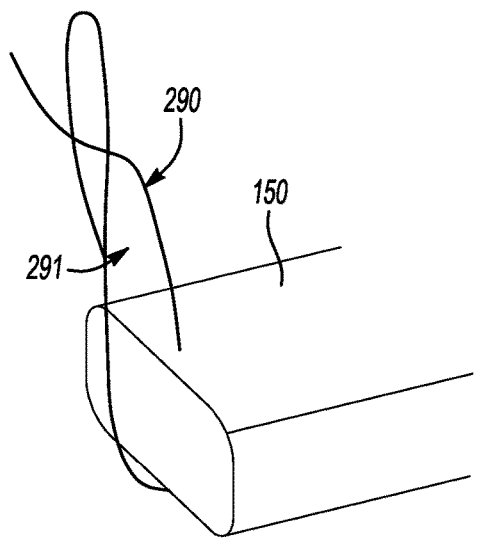
FIG. 21B demonstrates a double row suture technique.

FIGS. 21A and 21B schematically illustrate a single row (FIG. 21A, panel 1 and panel 2) and a double row (FIG. 21B) technique for cinching down suture 280 connecting a graft 150 to bone (not shown). As shown in FIG. 21A, Panel 1, a loop 281 of the suture 280 can be difficult to cinch down as suture links 282 tend to hang up on soft tissue and on intersecting links. A pusher 284 may be used to cinch down the loop 281, as demonstrated in FIG. 21A, Panel 2. Similarly, a suture 290 with a loop 291 can be passed and cinched down as a cinch loop and then fixed to bone with a knotless anchor (see FIG. 21B).

Figure 22A:
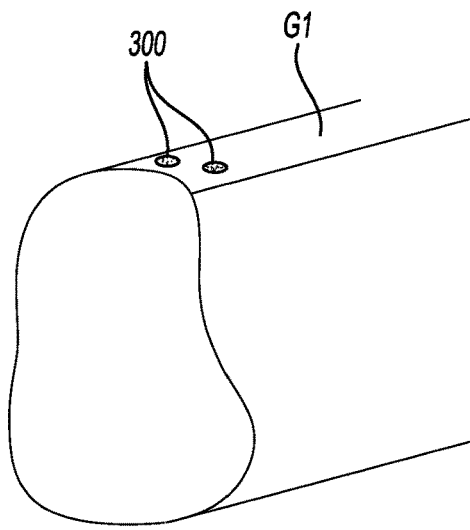
FIGS. 22A, 22B and 22C illustrate a dual dermal allograft technique for glenoid resurfacing plus superior capsule reconstruction.
Figure 22B:
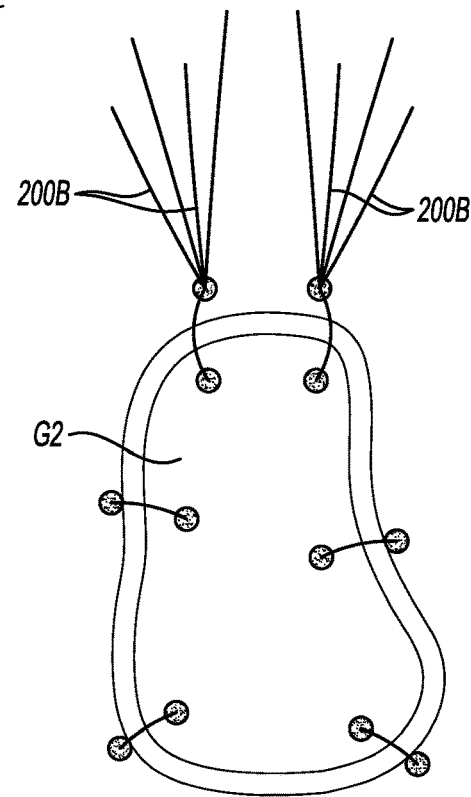
Figure 22C:
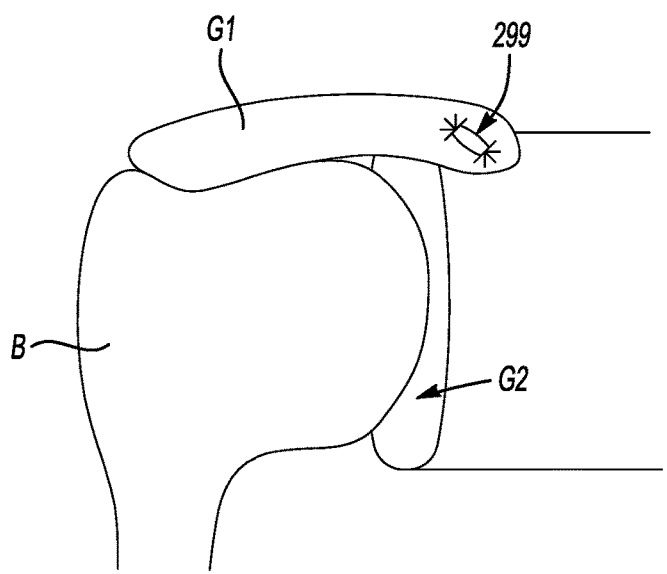

A dual graft allograft technique is schematically illustrated in FIGS. 22A-22C. This technique demonstrates a dual allograft for glenoid resurfacing plus superior capsular reconstruction. Therefore, an SCR graft G1 and a glenoid graft G2 are used. In some non-limiting embodiments, knotless anchors can be used inferiorly (e.g., (2) inferior, (2) mid, (2) superior), and superior anchors can be triple-loaded anchors. In some embodiments, coreless sutures may be used to allow three (3) sutures to fit through an eyelet of the anchors. The (2) superior anchors will be used to fix the upper part of the glenoid graft, plus the medial part of the superior capsular graft, such as by using a double pulley system 299 (see FIG. 22C). Exemplary double pulley system techniques are described in the $2^{nd}$ International Symposium on Operative and Biologic Treatments in Sports Medicine (June, 2007) (See Burkhart, ABSTRACT, "Repair of Subscapularis Tear"), Koo et al. (2009), The Journal of Arthroscopic and Related Surgery, 25 (11): 1343-1348), Arrigoni et al. (2007), The Journal of Arthroscopic and Related Surgery, 23(6): 675.e.1e (Technical Note). These teachings relating to the double pulley system used in reconstructive repair of joints, particularly rotator cuff repair, are incorporated herein by reference. In addition, reference is made to "The Cowboy's Companion, A Trail Guide for the Arthroscopic Shoulder Surgeon", 2012, Lippincott, Williams & Wilkins (2012), pg. 162 (FIG. 7.42), which demonstrates a double pulley system used to shuttle a dermal graft into a joint space of the body.

According to another non-limiting embodiment, and as part of a method for resurfacing the glenoid after performing capsular release, triple-loaded suture anchors 300 can be placed 3 to 4 mm medial to the "corner" of the superior glenoid (see FIG. 22A). After the glenoid graft fixation, there are still (2) sutures 200B in each superior anchor to use for a double pulley technique (see FIG. 22B). FIG. 22C illustrates the double pulley system 299 for fixation of the superior capsule reconstruction glenoid graft G1 and the glenoid graft G2 to the bone B.

Figure 23A:
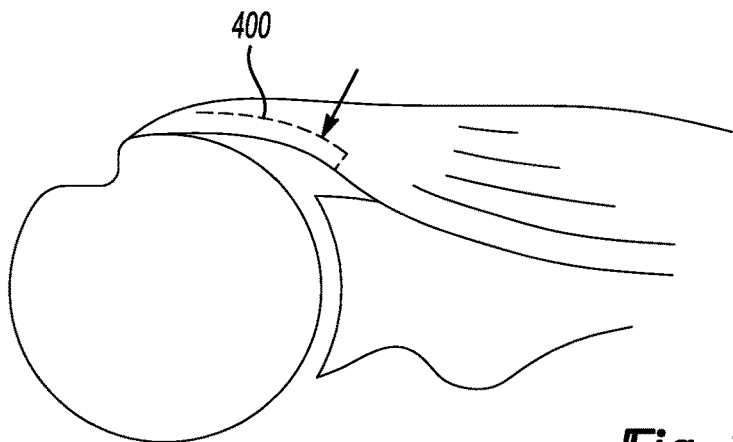
FIGS. 23A, 23B and 23C schematically illustrate reconstruction of an anterior capsule.
Figure 23B:
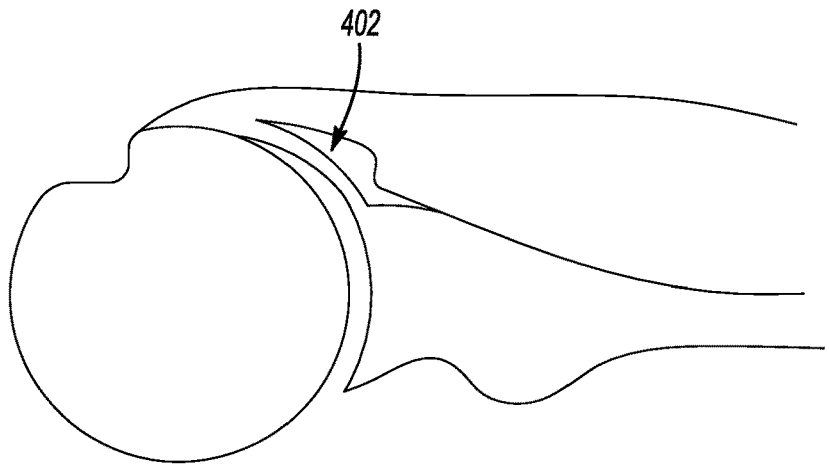
Figure 23C:
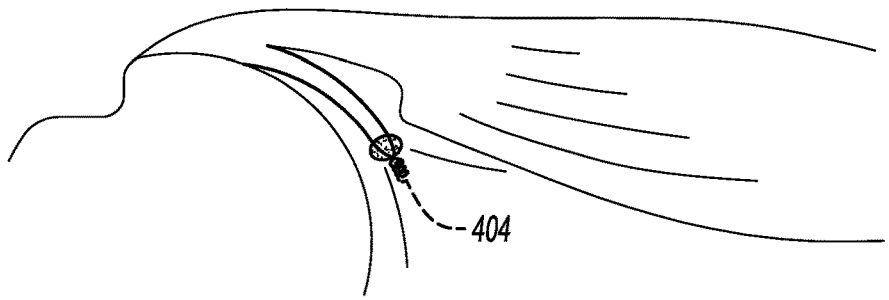

FIGS. 23A-23C illustrate a reconstruction of the anterior capsule by splitting the subscapularis tendon 400 (see dotted line) so that it can be used to substitute for the deficient anterior capsule. FIG. 23B illustrates the transfer of the split portion of the tendon over to the glenoid rim 402. FIG. 23C illustrates a close-up view of the split subscapularis reconstruction after it has been attached to the glenoid rim with a suture anchor 404. A graft could then be used to augment the reconstruction.

Figure 24A:
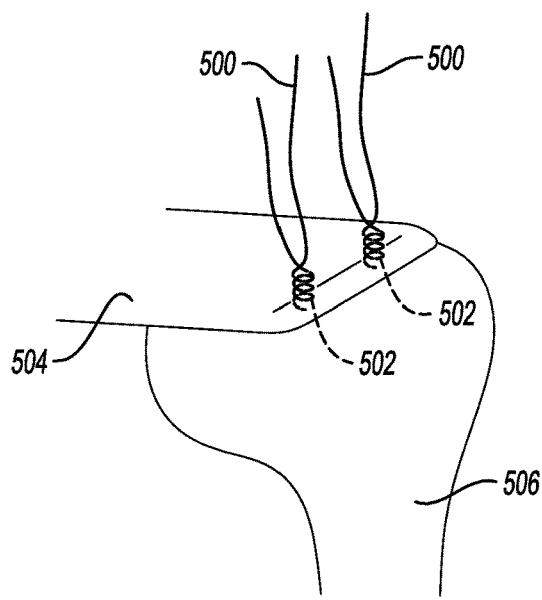
FIGS. 24A and 24B illustrate a linked, double row graft fixation.
Figure 24B:
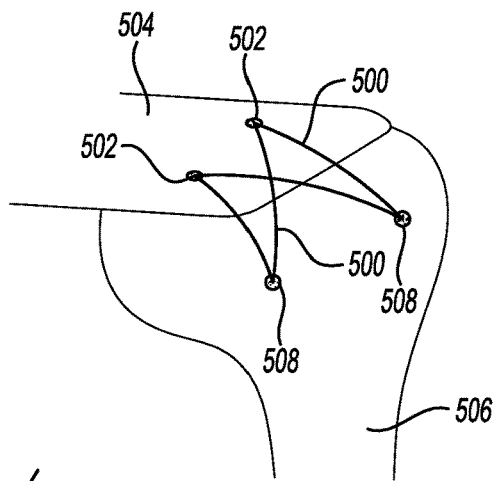

In yet another aspect of an exemplary reconstruction technique, a linked, double row graft fixation with sutures can be employed. As shown in FIG. 24A, sutures 500 from (2) medial row anchors 502 are placed and tied securing a graft 504 to the humerus 506. The suture limbs 500 from the medial anchors 502 may then crisscrossed and secured with lateral knotless anchors 508 (see FIG. 24B).

Figure 25A:
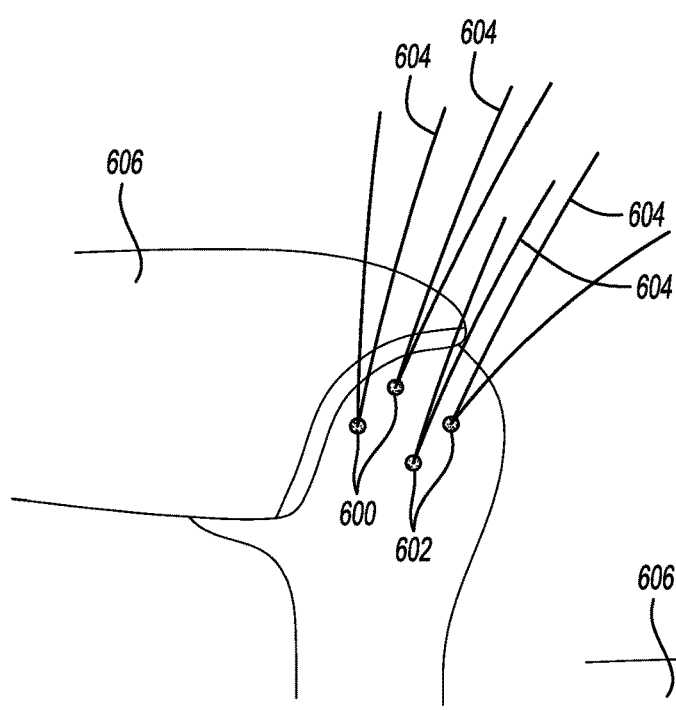
FIG. 25A illustrates sutures from (2) medial anchors and (2) lateral anchors prior to passing the sutures through a graft.
Figure 25B:
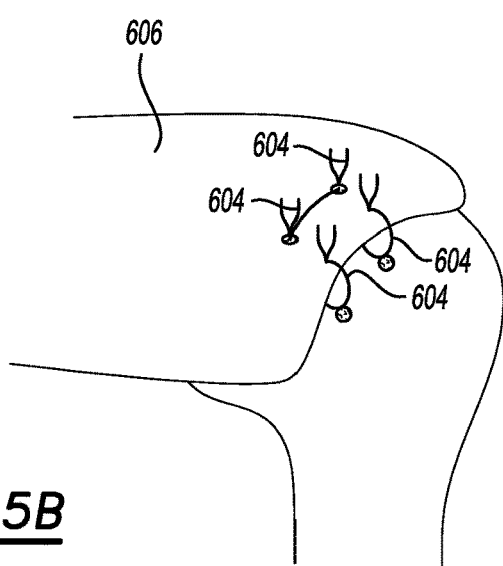
FIG. 25B shows the final configuration of the repair of FIG. 25A after the sutures have been passed and individually tied.

Another non-limiting embodiment, shown in FIGS. 25A and 25B, illustrates placement of (2) medial anchors 600 and (2) lateral anchors 602 prior to passing the sutures 604 through the graft 606. FIG. 25B shows the final configuration of the repair after the sutures 604 have been passed and individually tied.

Figure 26A:
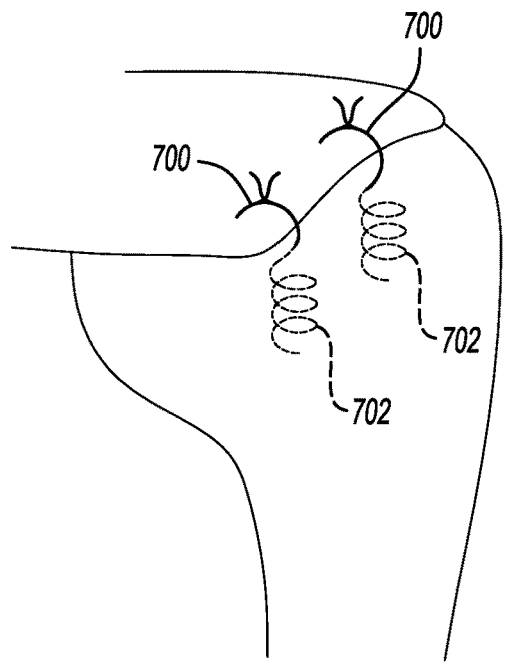
FIG. 26A shows a knotted fixation with suture and suture anchors.
Figure 26B:
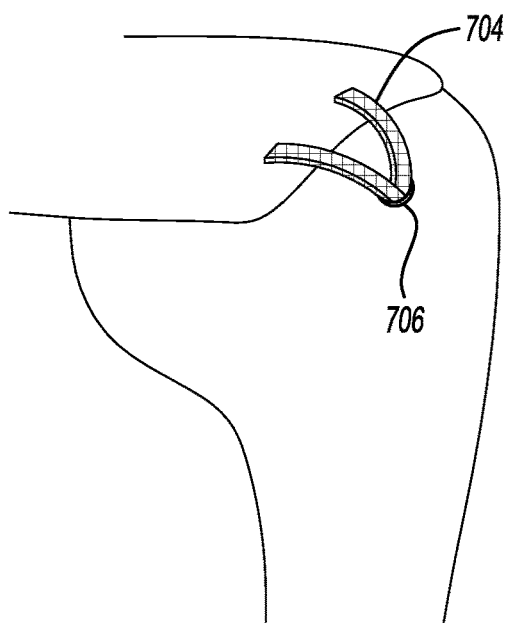
FIG. 26B shows a knotless fixation with suture tape.
Figure 26C:
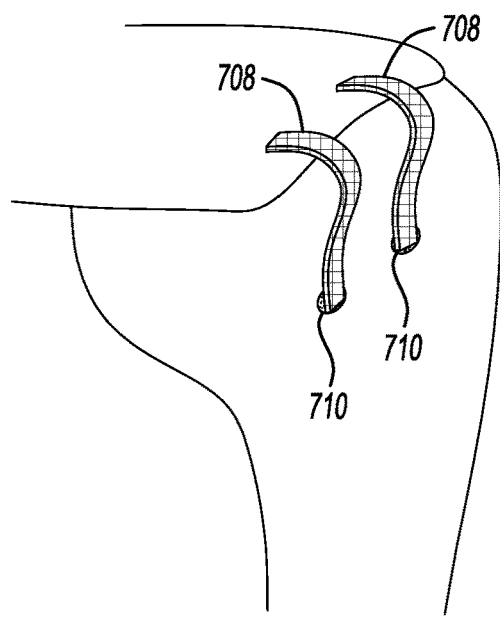
FIG. 26C shows fixation using cinch-loop sutures and knotless suture anchors.

FIGS. 26A-26B illustrate a knotted fixation (FIG. 26A) and a knotless fixation (FIG. 26B) using suture 700 and suture anchors 702. FIG. 26B shows a knotless fixation using suture tape 704. The single row fixation is shown to include a suture tape 704 passed as an inverted mattress suture and secured laterally with a knotless anchor 706. Multiple suture tape fixation points with knotless anchors may be used. FIG. 26C shows another knotless embodiment using cinch-loop sutures 708 fixated with knotless anchors 710.

A kit for joint kinematic reconstruction can also be provided. The kit may include, for example, the materials necessary for capsular reconstruction. In some embodiments, the kit would include:
1. At least (6) suture anchors (e.g., (2) knotted anchors and (4) knotless anchors, (2) of which can be pre-loaded with suture tape).
2. One or more dermal allografts. The dermal allograft, or other appropriate biologically compatible material, may be provided with a suture already passed through the graft, or instead, without suture passed through the graft.
3. Disposable drills, drill guides, punches, and taps for suture anchors.

Optionally, the kit could include an instructional insert to include, for example, instructive diagrams and/or describing the methodology provided herein to perform a kinematic reconstruction technique, such as for a capsular reconstruction.

FIGS. 27-31 schematically illustrate yet another exemplary joint kinematic reconstruction technique. The joint kinematic reconstruction technique of this particular embodiment is designed for performing superior capsular reconstructions of the glenohumeral joint.

Figure 27:
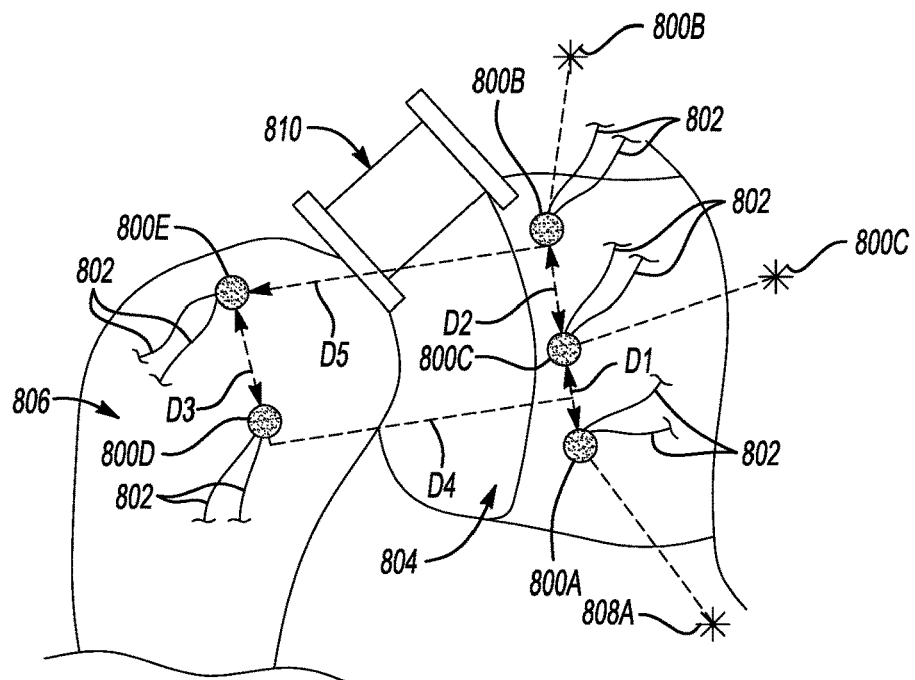
FIG. 27 schematically illustrate the implantation of suture anchors into a glenoid and humerus of an unstable glenohumeral joint.

Referring first to FIG. 27, after preparing the glenohumeral joint by debridement, creating bleeding bone beds, etc., a plurality of suture anchors 800 may be fixated within the glenohumeral joint for attaching various sutures 802 to the bone or bones of the unstable glenohumeral joint. After being fixated, the sutures 802 can be used to fixate a graft (see, e.g., feature 812 of FIG. 29) for stabilizing the glenohumeral joint.

Two or more suture anchors 800 may be positioned within each of a glenoid 804 and a humerus 806 of the glenohumeral joint. In an embodiment, three suture anchors 800A, 800B, and 800C are positioned in the glenoid 804 and two additional suture anchors 800D, 800E are positioned in the humerus 806. The use of three suture anchors in the glenoid 804 can help prevent bowstringing of the graft (see feature 812 of FIG. 29), which can result in the loss of contact between the graft 812 and the glenoid 804. In an embodiment, the third suture anchor 800C is utilized if the distance between the first and second suture anchors 800A and 800B is greater than about 20 mm. In another embodiment, each of the suture anchors 800A-800E is a knotless suture anchor (i.e., a suture anchor that does not require tying knots in order to fixate the graft to bone).

Each of the suture anchors 800A, 800B, and 800C that are implanted into the glenoid 804 may be inserted through their own respective percutaneous skin incisions 808A, 808B, and 808C. Inserting and tensioning out of the percutaneous skin incisions 808A-808C keeps the sutures 802 from each suture anchor 800A-800C separated, thereby simplifying suture management during the technique. The suture anchor 800A may be positioned at an anterior position of the glenoid 804, the suture anchor 800B may be positioned at a posterior position of the glenoid 804, and the suture anchor 800C may be positioned at an intermediate position that is between the anterior position of the suture anchor 800A and the posterior position of the suture anchor 800B. In an embodiment, at least one of the suture anchors 800A, 800B, and 800C are double loaded with sutures to provide double row construct options on the glenoid 804.

The suture anchors 800D and 800E of the humerus 806 may be inserted through a medially positioned cannula 810. The suture anchor 800D may be positioned at an anterior position of the greater tuberosity of the humerus 806, and the suture anchor 800E may be positioned at a posterior position of the greater tuberosity of the humerus 806. A third suture anchor may optionally be positioned into the humerus 806 at an intermediate position between the suture anchors 800D and 800E. In an embodiment, the third suture anchor is employed if the distance between the suture anchor 800D and the suture anchor 800E is relatively large (i.e., larger than about 20 mm). The suture anchors 800D and 800E (and, optionally, the third humeral suture anchor) may each carry two or more sutures and/or suture tapes in order to have enough sutures to complete double pulley constructs for shuttling the graft into the joint space. These additional suture can also be used for attaching the graft to the anterior (comma tissue) and posterior (infraspinatus) soft tissues, and/or for repairing all or part of the rotator cuff over the top of the graft 812.

A plurality of measurements are next taken between the various suture anchors 800A-800E in order to size the graft 812 that is to be used to reconstruct the superior capsule of the glenohumeral joint. A measuring technique similar to those shown in FIGS. 3A-3D or FIGS. 20A-20B, or any other measuring technique may be used to obtain the anterior-posterior distances between each of the three suture anchors 800A, 800B, and 800C, the anterior-posterior distances between the suture anchors 800D and 800E, and the medial-lateral distances between the medially placed suture anchors 800A, 800B, 800C of the glenoid 804 and the laterally placed suture anchors 800D, 800E of the humerus 806. For example, a first distance D1 may be measured between the suture anchor 800A and the suture anchor 800C, a second distance D2 may be measured between the suture anchor 800B and the suture anchor 800C, a third distance D3 may be measured between the suture anchor 800D and the suture anchor 800E, a fourth distance D4 may be measured between the suture anchor 800A and the suture anchor 800D, and a fifth distance D5 may be measured between the suture anchor 800B and the suture anchor 800E.

The measured distances D1 to D5 are used to size the graft 812. The graft 812 could include either an allograft or an autograft. In an embodiment, the graft 812 is an acellular dermal extracellular matrix.

Figure 28:
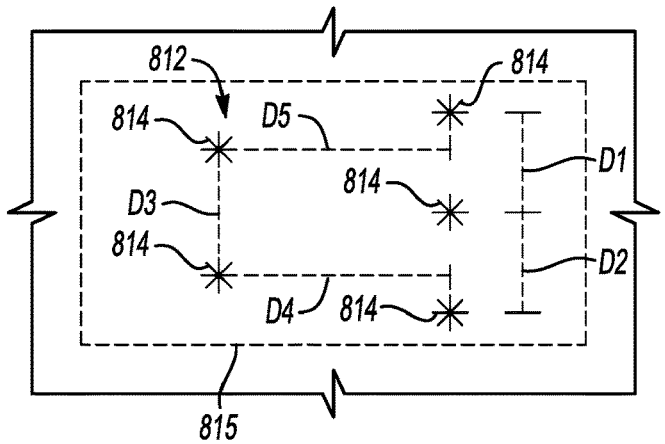
FIGS. 28 and 29 schematically illustrate the sizing and preparation of a graft for subsequent use in restoring the joint kinematics of the unstable glenohumeral joint.

As shown in FIG. 28, a multitude of marks 814 may be made on the graft 812 to designate the locations where the sutures 802 from the suture anchors 800A-800E will pass through the graft once it is positioned in situ. The location of the marks 814 are determined with reference to the measured distances D1 to D5. The surgeon may further select an appropriate distance between the marks 814 and the edges of the graft 812 to decrease the chances of the sutures 802 cutting through the graft 812. The graft 812 is then cut to the desired size (see dashed line 815) by removing excess material using a suitable cutting device.

Figure 29:
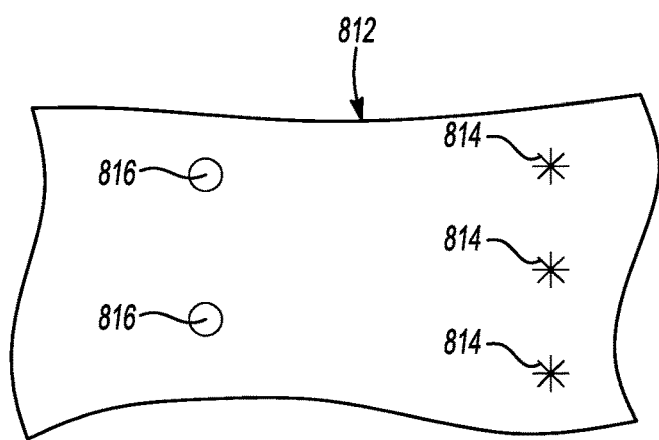

Referring now to FIG. 29, a hole 816 may be punched through the graft 812 at the marks 814 that are associated with the suture anchors 800D and 800E. The marks 814 associated with the suture anchors 800A, 800B, and 800C may or may not be punched to create a hole. The holes 816 allow the sutures 802 to slide relative to the graft 812 as the graft 812 is shuttled into position within the glenohumeral joint.

Figure 30:
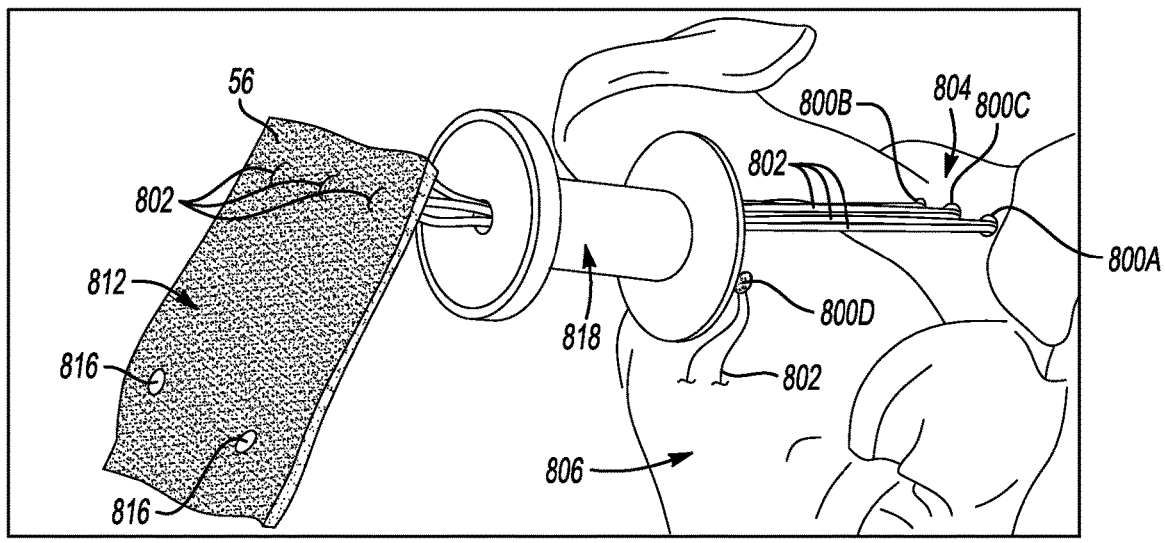
FIG. 30 schematically illustrates the retrieval and passage of multiple sutures from glenoid suture anchors through the graft.

As shown in FIG. 30, the graft 812 is next aligned and oriented at a location external to the glenohumeral joint, or outside of the skin of the body containing the joint, in a manner that mimics its implanted position. The sutures 802 from the suture anchors 800A, 800B, and 800C may then be retrieved through a laterally positioned cannula 818 and then inserted through the graft 812 at the location of the marks 814 that are associated with the suture anchors 800A, 800B, and 800C while the graft 812 is located outside of the glenohumeral joint. In an embodiment, the sutures 802 are retrieved from the joint one-by-one (i.e., sequentially), passed through the graft 812 (e.g., by using mattress stitches), shuttled into the suture anchor for completing the knotless mechanism and then shuttled back through their respective percutaneous skin incision 808, and then tensioned prior to shuttling an additional suture 802 through the cannula 818. The sutures 802 from the suture anchors 800D and 800E are not inserted through the graft 812 at this juncture of the technique.

The graft 812 may next be shuttled to a position inside the glenohumeral joint by slightly folding the graft 812 and inserting it through the cannula 818. The graft 812 is advanced by tensioning each of the sutures 802 until it is generally aligned over top of the suture anchors 800A, 800B, and 800C from which the sutures 802 extend.

If knotless suture anchors are not employed as the suture anchors 800A, 800B, and 800C, a double pulley technique as described above or a zipline technique can be used to shuttle the graft 812 into position inside the glenohumeral joint. An exemplary zipline technique may include, for example, retrieving one or more of the sutures 802 from each of the suture anchors 800A, 800B, and 800C, inserting the sutures 802 through the graft 812 at the location of the marks 814 that are associated with the suture anchors 800A, 800B, and 800C while the graft 812 is located outside of the glenohumeral joint, tying mulberry knots in the suture(s) 802 from the suture anchor 800C, and pushing the graft 812, such as by using a pushing tool, along the posteromedial and anteromedial suture 802 groups (i.e., along two 'zip-lines' from the sutures 802 of the suture anchors 800A and 800B) as the sutures 802 from the central glenoid anchor 800C are tensioned, thereby shuttling the graft 812 along the two zip-lines to its final position over the superior glenoid 804.

Figure 31:
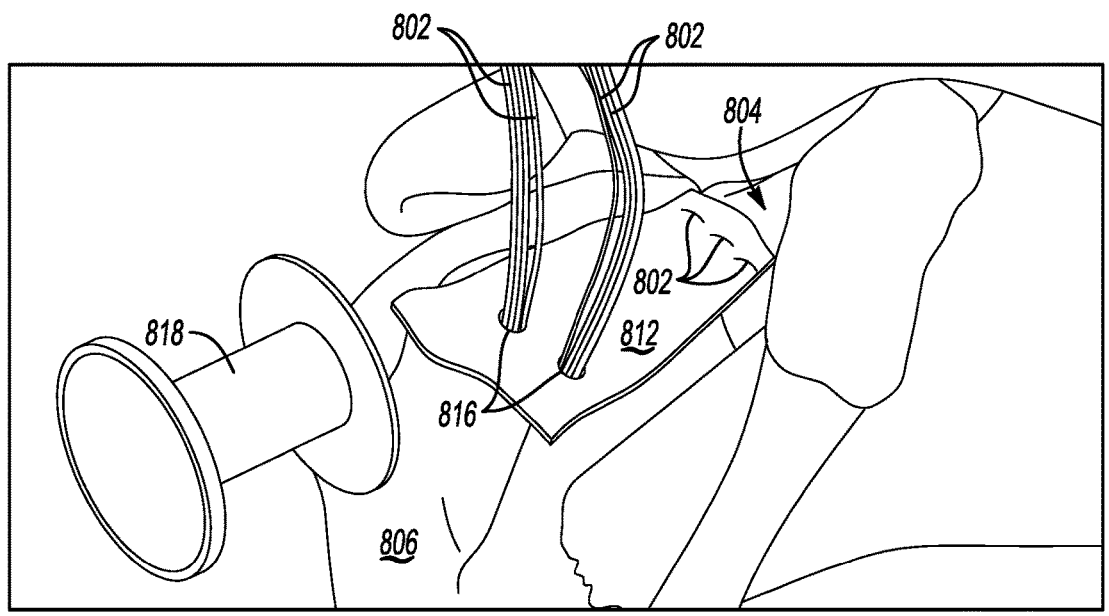
FIG. 31 schematically illustrates the retrieval and passage of multiple sutures from humeral suture anchors through the graft.

As shown in FIG. 31, the graft 812 may then be knotlessly fixated to the glenoid 804 using the sutures 802 from the suture anchors 800A, 800B, and 800C. Any knotless fixation technique can be used to fixate the graft 812 to the glenoid 804. Knotted techniques can also be utilized within the scope of this disclosure. Fixation of the graft 812 to the humerus 806 can be enhanced by using a knotted double-pulley technique to create a double mattress suture configuration between adjacent humeral suture anchors. Not only does this enhance fixation, but it sets the tension in the graft 812 by assuring that medial or lateral humeral fixation of the graft 812 occurs at exactly the points that were templated during the measurement of the graft 812. Fixation of the graft 812 to the humerus 806 may be further enhanced by adding additional humeral suture anchors.

With the graft 812 now located inside the glenohumeral joint and fixated relative to the glenoid 804, the sutures 802 from the suture anchors 800D and 800E of the humerus 806 may be retrieved and passed through the graft 812 at the location of the pre-punched holes 816. Passing the humeral sutures 802 after the graft 812 has been positioned within the joint and fixated to the glenoid 804 helps prevent the sutures 802 from becoming tangled or crossed with sutures from other anchors during this technique, thereby improving overall suture management.

Finally, the graft 812 may be fixated to the humerus 806 using a technique similar to that shown in FIGS. 8A and 8B, or any other knotless or knotted fixation technique. This completes the superior capsular reconstruction. Humeral fixation can optionally be augmented by adding additional humeral anchors and/or utilizing a double pulley fixation on the humeral side of the graft 812.

In an embodiment, a partial or complete repair of the rotator cuff may be done over the top of the graft 812 by utilizing any extra sutures in the humeral anchors 800A, 800B, and 800C to fix the rotator cuff, essentially "sandwiching" the graft 812 between the rotator cuff and the bone.

A kit for performing the joint kinematic reconstruction technique shown in FIGS. 27-31 can also be provided. The kit may include, for example, the materials necessary for capsular reconstruction. In an embodiment, the kit would include:

1. At least (6) knotless suture anchors, at least two of which are double loaded with sutures.
2. One or more dermal allografts.
3. A disposable punch for making holes in the dermal allograft.

In order that the disclosure described herein may be more fully understood, the following examples are set forth. It should be understood that these examples are for illustrative purposes only and are not to be construed as limiting this disclosure in any manner.

Example 1—Superior Capsular Reconstruction Method for Repair of Rotator Cuff Tear/SRC, Patient 1

This example describes one non-limiting embodiment of an exemplary capsular reconstruction method.

An active 64 year old female in excellent general health presented with shoulder pain of 5 years duration, along with increasing weakness that is beginning to restrict her activities, which include golf, gardening, and yard work.

On exam, the patient was able to raise her arm overhead, but was very weak. She was not able to hold up a half gallon of milk and take it out of the refrigerator. X-rays showed proximal migration of the humerus under the acromion, but no arthritic changes.

The patient had been advised that remedy of the problem required a reverse total shoulder replacement. Patient concern about the relatively high rate of complications with this procedure as well as the activity restrictions that would be required if she underwent this procedure prompted her to seek alternative advise.

Alternative shoulder surgery was performed as follows:

A partial rotator cuff repair was performed on the parts of the rotator cuff that were reparable (in this case, this included the subscapularis tendon and half of the infraspinatus tendon). A posterior interval slide was performed, but a complete repair of the rotator cuff was not possible. A superior capsular reconstruction was performed as described in the foregoing sections, using a dermal allograft. Partial repair of the rotator cuff over the top of the dermal graft was also performed. The surgery was performed on an outpatient basis, and the patient went home the same day. She had minimal pain after her surgery, and hardly needed any pain medication. She wore a sling for 6 weeks, and then began a program of passive range of motion. At 4 months postoperatively, the patient was seen, and found to have strength on the operated side to almost a normal level and equal to the other side. She reported to have no pain; and had complete range of motion of the shoulder.

The patient demonstrated a rapid recovery of strength not demonstrated with other options, including arthroplasty and arthroscopic partial repair. In addition, the procedure performed was much less costly than a shoulder replacement without the added risks of significantly higher complications with reverse total shoulder replacement. In addition, the patient had much less pain than she would have had with the replacement procedure.

Importantly, the patient did not eliminate any future treatment options by having this procedure. If it were to fail at some point in the future, all other treatment options would still be available to her, including reverse total shoulder replacement.

The particularly significant aspects of the present example, as relates the method in providing repair of a significant rotator cuff repair using superior capsular reconstruction as described herein included:

1. The graft "re-centers" the humeral head on the superior glenoid, and thereby restores force couples acting about the joint.
2. The method includes a step wherein exposure of the superior glenoid is improved for purposes of enhancing visibility during the procedure, by way of a posterior interval slide. Anterior interval slide and/or capsular release (underneath the rotator cuff) can also enhance exposure of the superior glenoid in some cases).
3. Superior placement of a graft to the surgical area is provided by employing a double pulley technique. The double pulley techniques provides advantages in that the double pulley technique automatically shuttles the graft directly over the top of the anchors to which the graft need to be secured, because the sutures that are used to form the double pulley come from those anchors.
4. The method provides for the delivery and subsequent tensioning of a lateral part of the graft material, such as through the use of a retriever/tensioner or a knot pusher with an oversized hole to accommodate suture tape.
5. The force couples achieved with the present technique are enhanced though the inclusion of a step wherein a partial closure/repair of the rotator cuff is made so as to bring the rotator cuff over the top of the graft. This partial closure/repair is achieved using side-to-side margin convergence sutures. In this manner, the graft remains visible through the residual defect of the cuff.
6. Use of a dermal allograft as the graft of choice in the repair process yielded significant improvements in patient outcome. Particularly, patients having undergone the present procedure wherein a dermal allograft was used were observed to have dramatic improvements in strength, active motion, and pain relief compared to most other surgical approaches, yet with the decreased morbidity of a minimally invasive arthroscopic procedure.
7. The graft materials that may be employed as part of the reconstruction/repair method may include any number of biologic (i.e., Arthroflex dermal allograft; scaffold impregnated with cells and/or tissue material) or synthetic material (e.g. polymer scaffold impregnated with biologic enhancement factors).

Example 2—Clinical Results Using SCR, Patient 2

This non-limiting example demonstrates the use of a reconstructive methodology in a human patient having an irreparable rotator cuff tear.

A rotator cuff tear is considered irreparable if, in the opinion of the attending surgeon, the tear cannot be fully mobilized to the extent that the tendon can be fully repaired back to its normal bone attachments.

A male patient, age 38, weight 220 pounds, in otherwise good general physical condition, presented with inability to raise his arm after a series of shoulder injuries that had occurred in the course of his occupation as a laborer in the oilfields. The patient could not raise his arm above 30 degrees, and he had profound weakness, as well as constant pain in the shoulder. He was not educationally equipped to do any occupation except manual labor.

Shoulder surgery was performed according to the following protocol. A partial repair of the rotator cuff was performed. The subscapularis and the infraspinatus were repaired. The supraspinatus was irreparable. A biceps tenodesis was performed, followed by a superior capsular reconstruction with dermal allograft.

The patient was hospitalized for a short period and released. The patient's surgery was performed on an outpatient basis and he was released after 2 hours in the recovery room. He was kept in a sling for 6 weeks, and then a passive range of motion program was begun, followed by strengthening at 4 months postoperatively. He returned to regular duty at work at 6 months postoperatively. I last saw him at 10 months post-op, at which point he had full range of motion and normal strength. In this case, the patient was not a candidate for a reverse total shoulder replacement because of his young age and because of his high demand level as a manual laborer. In this case, a young high demand individual was returned to an active productive life by this procedure, whereas other surgical options were highly unlikely to be able to provide such a result.

The patient was allowed to heal and a follow-up on the status of the patient's surgery was performed. Compared to other rotator cuff repair approaches, the range of motion was significantly better (greater) than that observed typically in patients having undergone more conventional rotator cuff repair procedures. Care should be taken not to allow the anchors to penetrate the articular surface, as such often results in the patient developing an arthritic shoulder.

Example 3—Fixation of Graft by Linked Double Row Sutures, Patient 3

This non-limiting example illustrates the use of sutures (rather than suture tape) to create double row fixation of the lateral part of the graft.

A 45 year old female injured her shoulder when she fell down her front porch steps. She presented with pain and weakness with difficulty lifting the arm overhead.

Surgery was performed arthroscopically on an outpatient basis. The tear demonstrated questionable tendon quality, and it was felt that medial knots would be stronger than a knotless technique in this patient. Medial suture anchors were first passed. They were then individually passed through the graft and tied as mattress sutures. The suture limbs were then secured just lateral to the graft with 2 knotless suture anchors.

The surgery was performed on an outpatient basis and she went home the same day. In this case, a knotted technique was used because of the greater biomechanical strength of fixation with medial knots.

She wore a sling for 6 weeks, and then started on a stretching program followed by a strengthening program at 4 months post-op. She was allowed to return to golf at 9 months post-op. When she was last seen in the office at 9 months post-op, she had essentially a normal exam.

Example 4—SCR/Single Row Repair with Graft, Patient 4

The patient is a small (under 5 feet tall), 70 year old female with chronic shoulder pain and progressive weakness. The patient indicated pain with overhead motion even though full motion was demonstrated. X-rays show proximal migration of the humerus due to a massive rotator cuff tear.

Arthroscopic superior capsular reconstruction was performed using a dermal allograft. Because of the fact that her greater tuberosity of the humerus was so small, a single row repair was done as there was not enough bone surface to implant two rows of suture anchors.

The patient went home two hours after her surgery. At 6 weeks post-op her sling was discontinued. She resumed gardening at 4 months postop.

This case illustrates an example in which there was not enough room on the bone footprint to place a double row of anchors, so single row repair was done and yielded satisfactory results.

Example 5—Use of a Double Grafting Procedure to Treat a Combination of Degenerative Arthritis of the Shoulder and Massive Irreparable Rotator Cuff Repair, Patient 5

This non-limiting example presents a prophetic surgical method for clinically managing a 40 year old athletic male who had been involved in a motor vehicle accident 3 years earlier. He was in a coma for 3 weeks, so nondisplaced fractures of the proximal humerus combined with massive rotator cuff tear were not treated initially. After he had regained consciousness and was dismissed to physical rehabilitation, his shoulder improved to the point that he declined further treatment. Two years later, he presented to the clinic with severe shoulder pain, loss of 30% of his active and passive range of motion, and significant weakness.

X-rays showed degenerative arthritis of the shoulder. MRI scan confirmed a massive rotator cuff tear. The patient was considered to be too young and too active for consideration of reverse total shoulder arthroplasty, but the arthritis was too far advanced for a simple arthroscopic debridement to achieve any pain relief.

A biologic glenoid resurfacing with dermal allograft was used to treat the patient's arthritis, in combination with superior capsular reconstruction with a separate dermal allograft to treat the massive rotator cuff tear. The procedure was performed arthroscopically.

First a capsular release was performed in order to create enough suppleness in the joint for all the various arthroscopic manipulations and procedures to be done. Then the biologic resurfacing of the glenoid was performed, attaching a templated dermal allograft to the periphery of the glenoid with 6 suture anchors after arthroscopically shuttling the graft into the joint. Then a second dermal allograft was fashioned to cover the defect in the rotator cuff. The second graft was shuttled into the shoulder where it was fixed to the superior glenoid with 2 suture anchors and to the greater tuberosity of the humerus with 4 suture anchors.

This case represents a method for treating a combination of shoulder arthritis and a massive cuff tear in a way that avoids total joint replacement. By preserving the patient's joint for many more years with this procedure, the patient could potentially maintain a vigorous lifestyle until reaching a more appropriate age for total shoulder replacement.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method for reconstructing a glenohumeral joint, comprising:
    inserting two or more suture anchors into a glenoid of the glenohumeral joint;
    inserting two or more suture anchors into a humerus of the glenohumeral joint;
    measuring a first distance either between a first suture anchor of the suture anchors inserted into the glenoid and a second suture anchor of the suture anchors inserted into the glenoid or between a first suture anchor of the suture anchors inserted into the humerus and a second suture anchor of the suture anchors inserted into the humerus;
    measuring a second distance either between the first suture anchor inserted into the glenoid and the first suture anchor inserted into the humerus or between the second suture anchor inserted into the glenoid and the second suture anchor inserted into the humerus;

sizing a graft based at least on the first distance and the second distance;

retrieving a first suture from one of the suture anchors inserted into the glenoid;

passing the first suture through a graft while the graft is positioned away from the glenohumeral joint;

retrieving a second suture from one of the suture anchors inserted into the humerus;

passing the second suture through the graft;

shuttling the graft through a cannula to the glenohumeral joint;

fixating the graft to the glenoid using the first suture; and fixating the graft to the humerus using the second suture.

2. The method as recited in claim 1, wherein inserting the two or more suture anchors into the glenoid includes:

inserting the first suture anchor at an anterior position of the glenoid; and inserting the second suture anchor at a posterior position of the glenoid.

3. The method as recited in claim 2, wherein inserting the suture anchors into the glenoid includes:

inserting a third suture anchor between the first suture anchor and the second suture anchor of the glenoid.

4. The method as recited in claim 1, wherein inserting the two or more suture anchors into the glenoid includes:

passing each of the suture anchors for the glenoid individually through a skin incision.

5. The method as recited in claim 1, wherein inserting the two or more suture anchors into the humerus includes:

inserting the first suture anchor at an anterior position of the humerus; and inserting the second suture anchor at a posterior position of the humerus.

6. The method as recited in claim 5, wherein the suture anchors inserted into the humerus are passed individually through a second cannula.

7. The method as recited in claim 6, wherein the cannula through which the graft is shuttled is a laterally positioned cannula and the second cannula is a medially positioned cannula.

8. The method as recited in claim 1, wherein the first distance is measured between the first and second suture anchors inserted into the glenoid and the second distance is measured between the first suture anchor inserted into the glenoid and the first suture anchor inserted into the humerus, and wherein the method further comprises:

measuring a third distance between the first and second suture anchors inserted into the humerus; and measuring a fourth distance between the second suture anchor inserted into the glenoid and the second suture anchor inserted into the humerus;

wherein sizing the graft is based on the first distance, the second distance, the third distance, and the fourth distance.

9. The method as recited in claim 8, wherein sizing the graft includes making the graft larger than the size indicated by the first distance, the second distance, the third distance, and the fourth distance.

10. The method as recited in claim 9, wherein sizing the graft includes making the graft larger than the size indicated by the first distance, the second distance, the third distance, and the fourth distance by approximately 5 mm in each direction.

11. The method as recited in claim 8, wherein sizing the graft includes marking the graft to indicate the locations where the first suture and the second suture are to pass through the graft.

12. The method as recited in claim 8, comprising, after sizing the graft, cutting the graft to remove excess material.

13. The method as recited in claim 12, comprising punching a hole through the graft prior to passing the first suture or the second suture through the graft.

14. The method as recited in claim 1, wherein fixating the graft to the glenoid includes knotlessly fixating the graft to the glenoid, and wherein fixating the graft to the humerus includes knotlessly fixating the graft to the humerus.

15. The method as recited in claim 1, wherein the graft is an acellular dermal extracellular matrix.

16. The method as recited in claim 1, wherein the second suture is retrieved and passed through the graft prior to shuttling the graft through the cannula to the glenohumeral joint.

17. The method as recited in claim 1, wherein the second suture is retrieved and passed through the graft after shuttling the graft through the cannula to the glenohumeral joint.

18. The method as recited in claim 1, wherein the graft is shuttled through the cannula to the glenohumeral joint prior to inserting the suture anchors into the humerus.

19. The method as recited in claim 1, wherein the graft is shuttled through the cannula to the glenohumeral joint after inserting the suture anchors into the humerus.

20. The method as recited in claim 1, wherein the first distance is measured between the first and second suture anchors inserted into the glenoid and the second distance is measured between the first suture anchor inserted into the glenoid and the first suture anchor inserted into the humerus, and wherein the method further comprises:

measuring a third distance between the first and second suture anchors inserted into the humerus; and wherein sizing the graft is based on the first distance, the second distance, and the third distance.

* * * * *